(12) United States Patent
Fujitaka et al.

(10) Patent No.: US 8,847,179 B2
(45) Date of Patent: Sep. 30, 2014

(54) TREATMENT PLANNING APPARATUS AND PARTICLE THERAPY SYSTEM

(75) Inventors: Shinichiro Fujitaka, Hitachi (JP);
Yusuke Fujii, Hitachi (JP); Rintaro Fujimoto, Hitachinaka (JP); Kazuo Hiramoto, Hitachiota (JP); Hiroshi Akiyama, Hitachiota (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 13/448,553

(22) Filed: Apr. 17, 2012

(65) Prior Publication Data
US 2012/0264998 A1    Oct. 18, 2012

(30) Foreign Application Priority Data

Apr. 18, 2011 (JP) ................................. 2011-091660

(51) Int. Cl.
*G21K 5/04* (2006.01)
*A61N 5/10* (2006.01)

(52) U.S. Cl.
CPC ....... *A61N 5/1043* (2013.01); *A61N 2005/1087* (2013.01); *A61N 5/1036* (2013.01); *A61N 5/1045* (2013.01)
USPC ............. 250/492.3; 250/492.1; 600/1; 700/1; 700/61; 700/253

(58) Field of Classification Search
USPC ............... 250/396 R, 397, 398, 491.1, 492.1, 250/492.3; 700/1, 61, 253; 600/1, 2, 3
See application file for complete search history.

(56) References Cited

U.S. PATENT DOCUMENTS

| | | | |
|---|---|---|---|
| 6,265,837 B1 | 7/2001 | Akiyama et al. | |
| 2001/0022502 A1* | 9/2001 | Akiyama et al. | 315/503 |
| 2008/0067401 A1 | 3/2008 | Harada | |
| 2012/0119105 A1* | 5/2012 | Iwata | 250/396 ML |
| 2013/0053617 A1 | 2/2013 | Pu et al. | |

FOREIGN PATENT DOCUMENTS

| | | |
|---|---|---|
| JP | 11-253563 A | 9/1999 |
| JP | 3518270 B2 | 2/2004 |
| JP | 2012-524507 A | 10/2012 |

OTHER PUBLICATIONS

S. Minohara et al. "Recent Innovations in Carbon-Ion Radiotherapy", Journal of Radiation Research, vol. 51, No. 4, Jun. 11, 2010, pp. 385-392.

(Continued)

*Primary Examiner* — Nicole Ippolito
(74) *Attorney, Agent, or Firm* — Mattingly & Malur, PC

(57) ABSTRACT

A charged particle beam reduces treatment time in the uniform scanning or in the conformal layer stacking irradiation. In the uniform scanning, an optimum charged particle beam scan path for uniformly irradiating a collimator aperture area is calculated. In the conformal layer stacking irradiation, an optimum charged particle beam scan path for uniformly irradiating a multi-leaf collimator aperture area of each layer for each of the layers obtained by partitioning the target volume is calculated. Alternatively, a minimum irradiation field size that covers the multi-leaf collimator aperture area of each layer is calculated, and a scan path corresponding to the irradiation field size, prestored in a memory of a particle therapy control apparatus, is selected. The charged particle beam scan path is optimally changed in the lateral directions in conformity with the collimator aperture area in the uniform scanning or in each layer in the conformal layer stacking irradiation.

14 Claims, 19 Drawing Sheets

(56) References Cited

OTHER PUBLICATIONS

V. A. Anferov, "Scan pattern optimization for uniform proton beam scanning", Med. Phys. 36 (8), Aug. 2009, pp. 3560-3567.

S. Yonai et al., "Evaluation of beam wobbling methods for heavy-ion radiotherapy", Med Phys. 35 (3), Mar. 2008, pp. 927-938.

T. Kanai et al., "Commissioning of a conformal irradiation system for heavy-ion radiotherapy using a layer-stacking method", Med. Phys. 33 (8), Aug. 2006, pp. 2989-2997.

M. Komori et al., "Optimization of Spiral-Wobbler System for Heavy-Ion Radiotherapy", Japanese Journal of Applied Physics, vol. 43, No. 9A, 2004, pp. 6463-6467.

* cited by examiner

FIG. 4
(a)
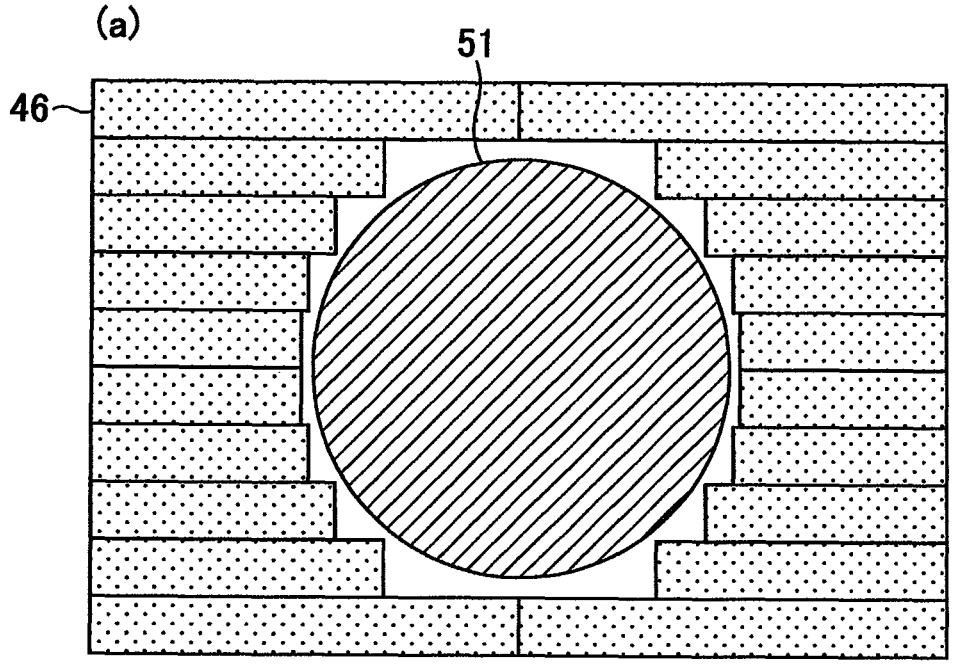
(b)
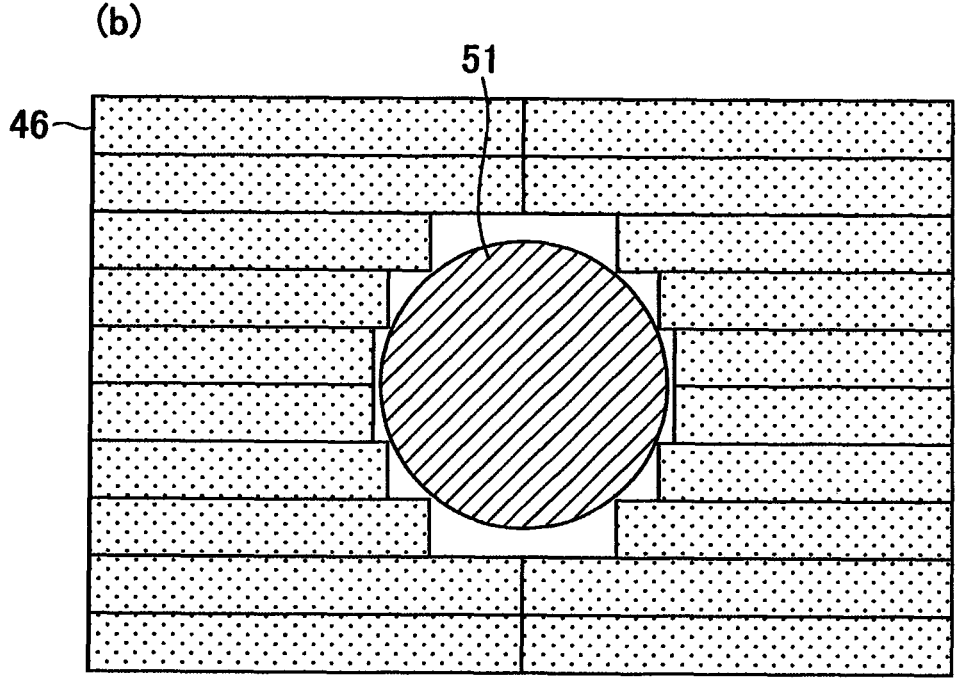

| LAYER | IRRADIATION AMOUNT |
|---|---|
| 1 | 40 |
| 2 | 15 |
| 3 | 10 |
| 4 | 8 |
| 5 | 6 |
| 6 | 5 |
| 7 | 5 |
| 8 | 4 |

STARTING POINT

ENDING POINT

FIG. 12
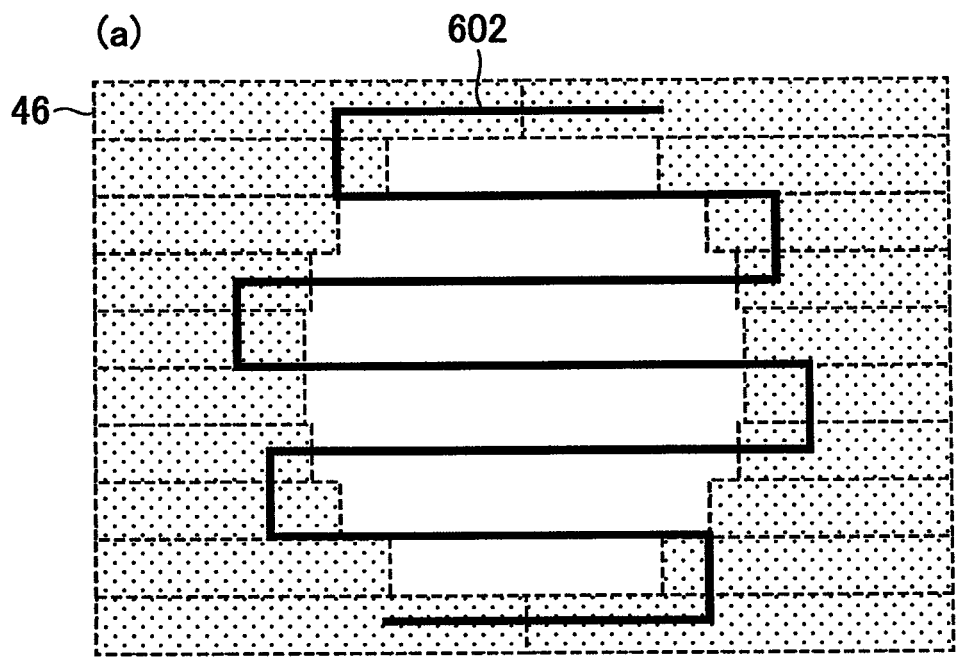
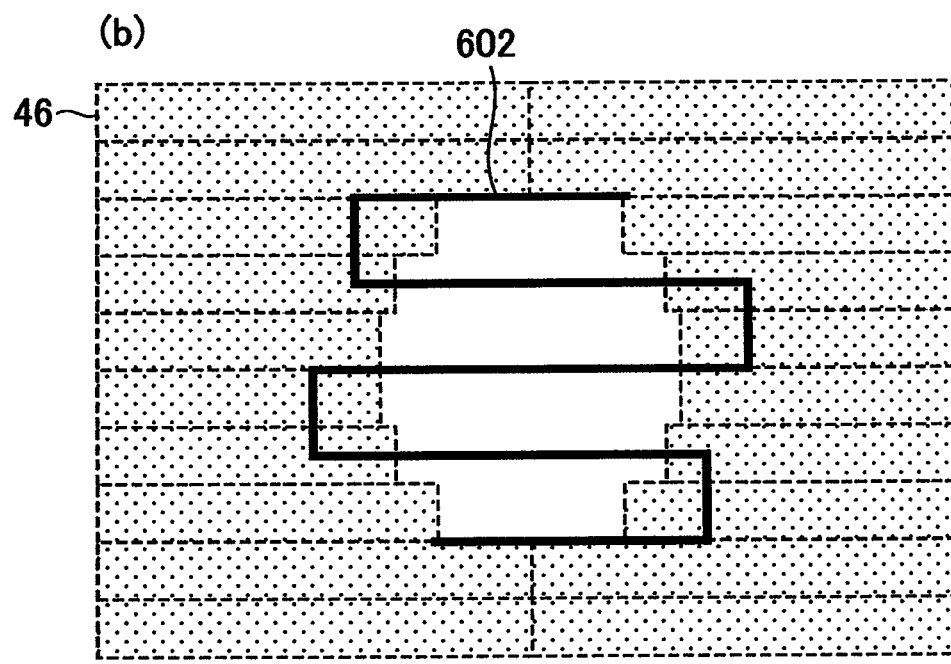

FIG. 13

|   | EXCITATION CURRENT VALUE X (A) | EXCITATION CURRENT VALUE Y (A) |
|---|---|---|
| 1 | 480 | −480 |
| 2 | 480 | −420 |
| 3 | −480 | −420 |
| 4 | −480 | −360 |
| ⋮ | ⋮ | ⋮ |

FIG. 15
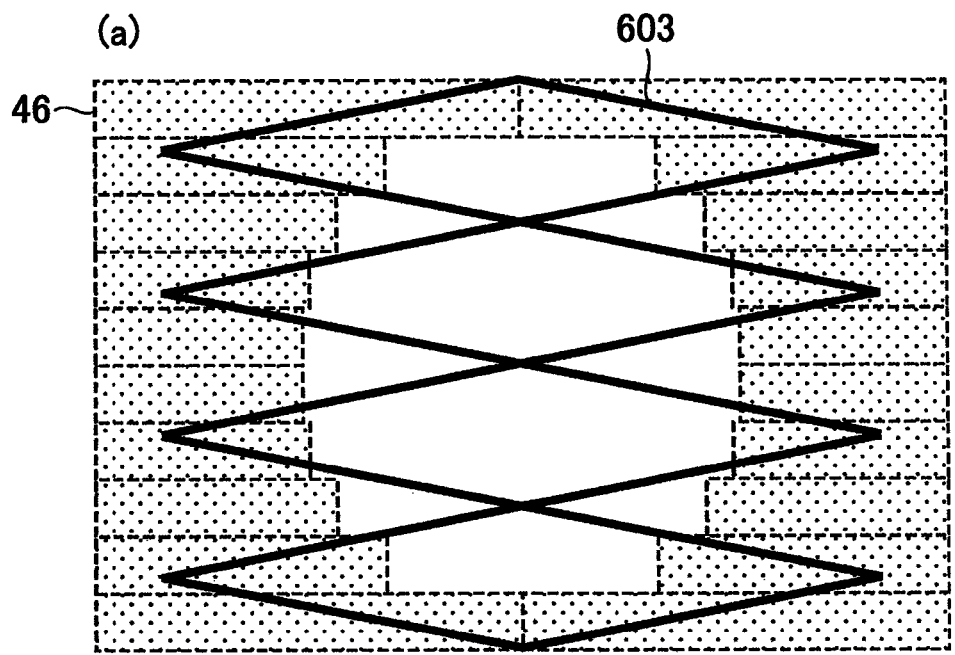
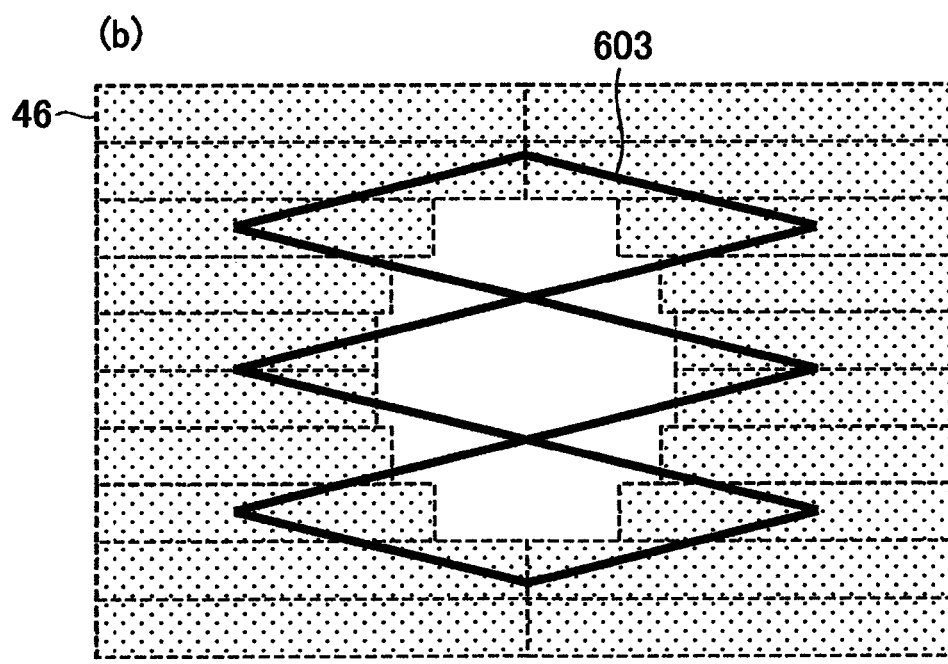

FIG. 16
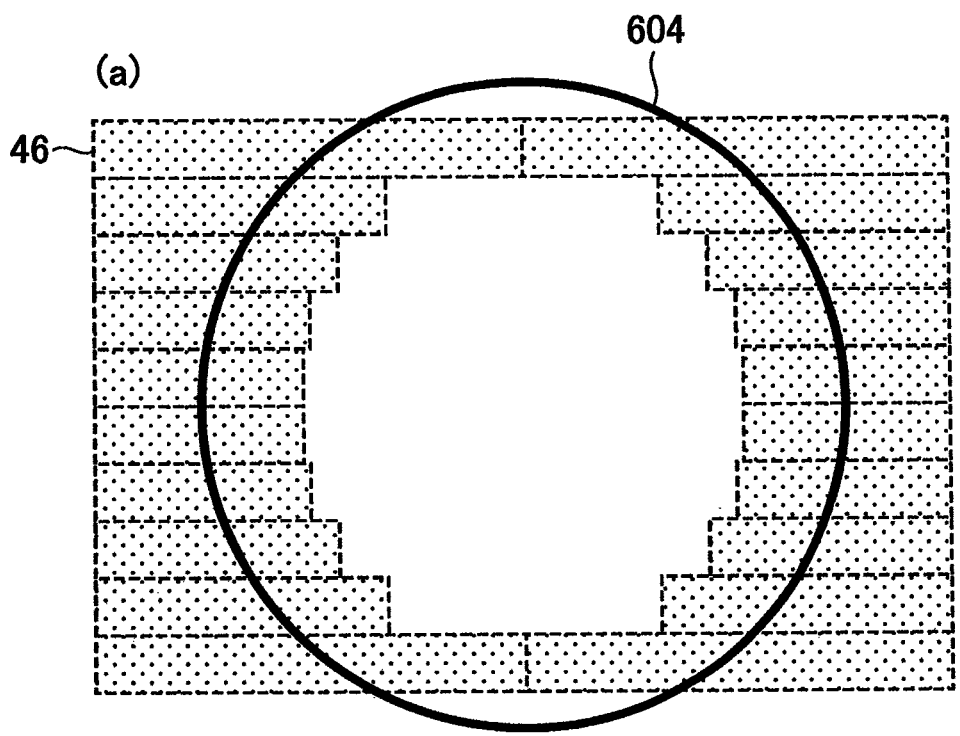
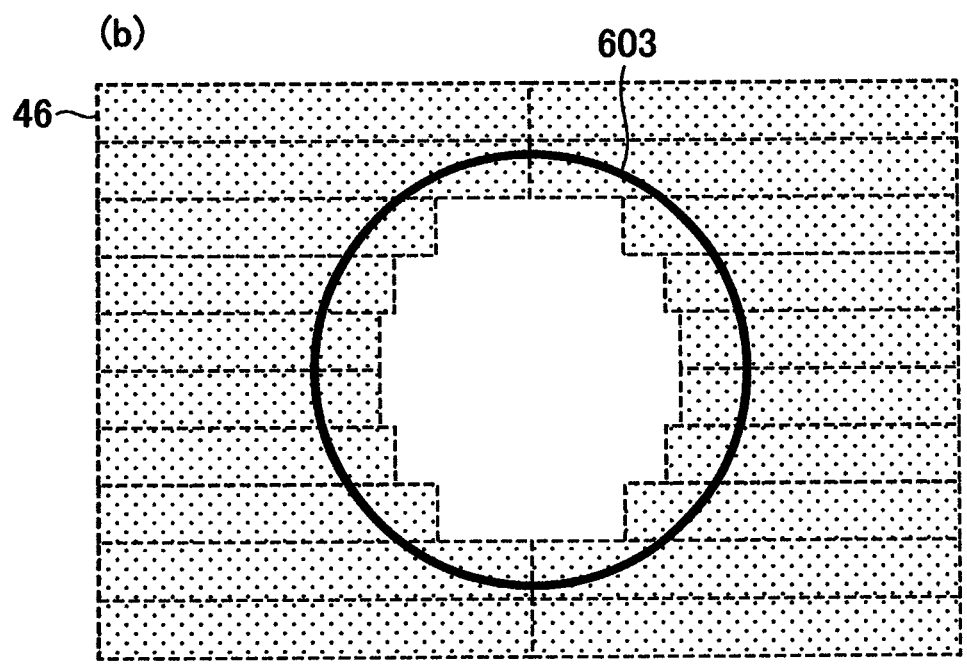

FIG. 17
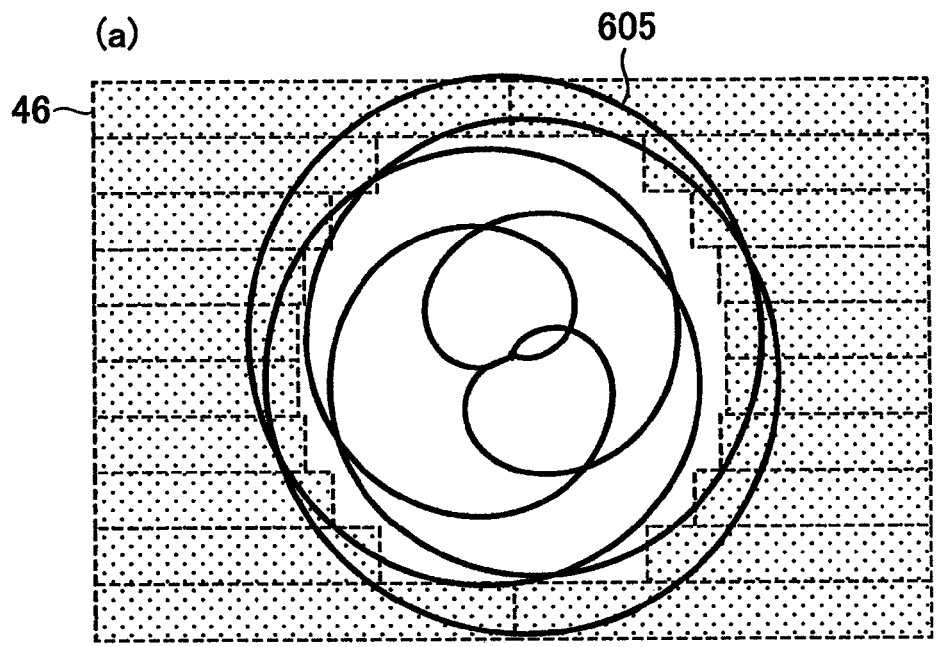
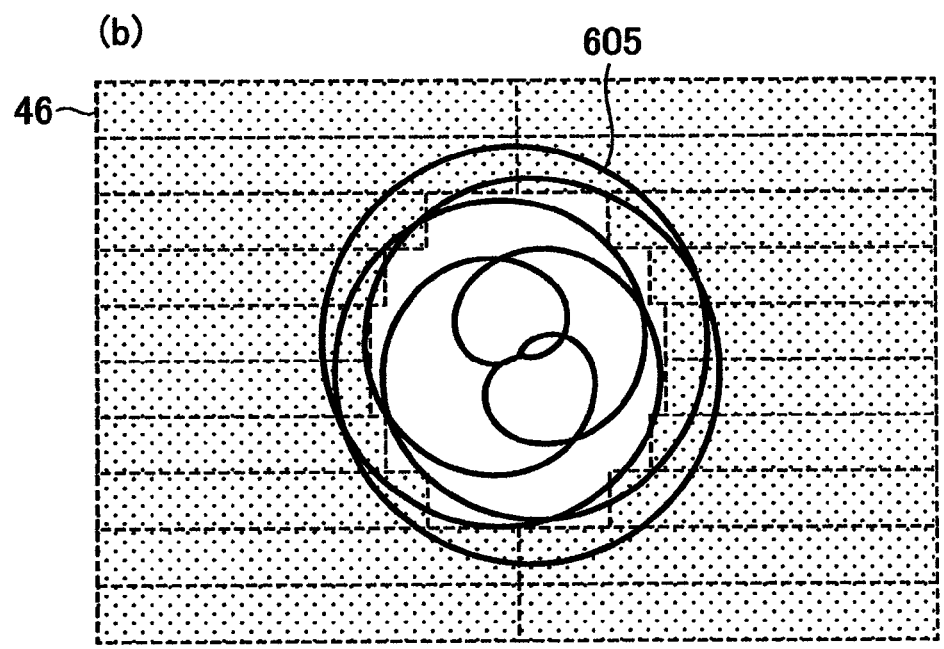

FIG. 18
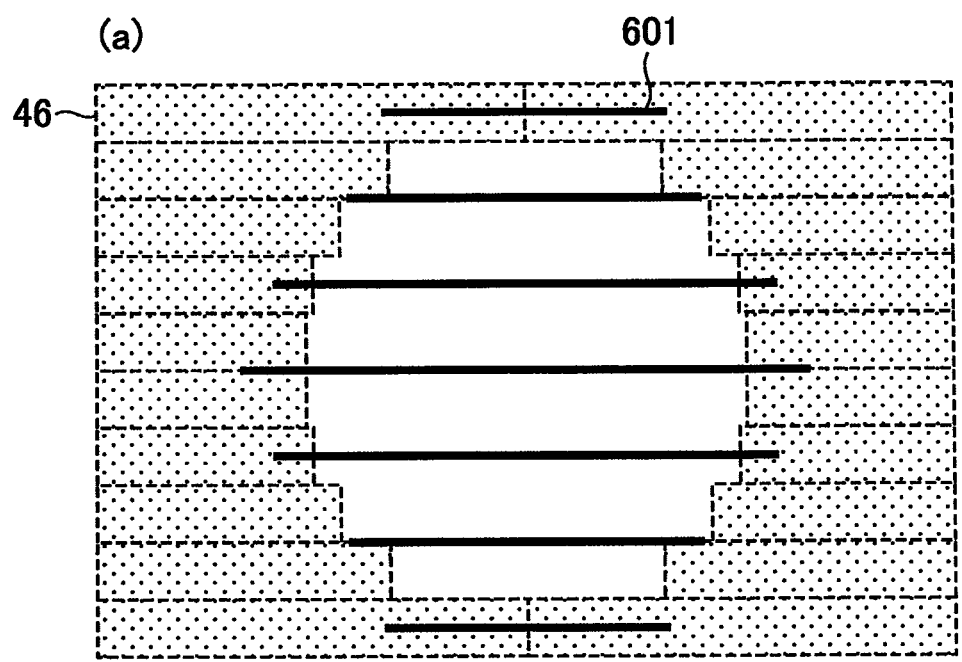
(a)
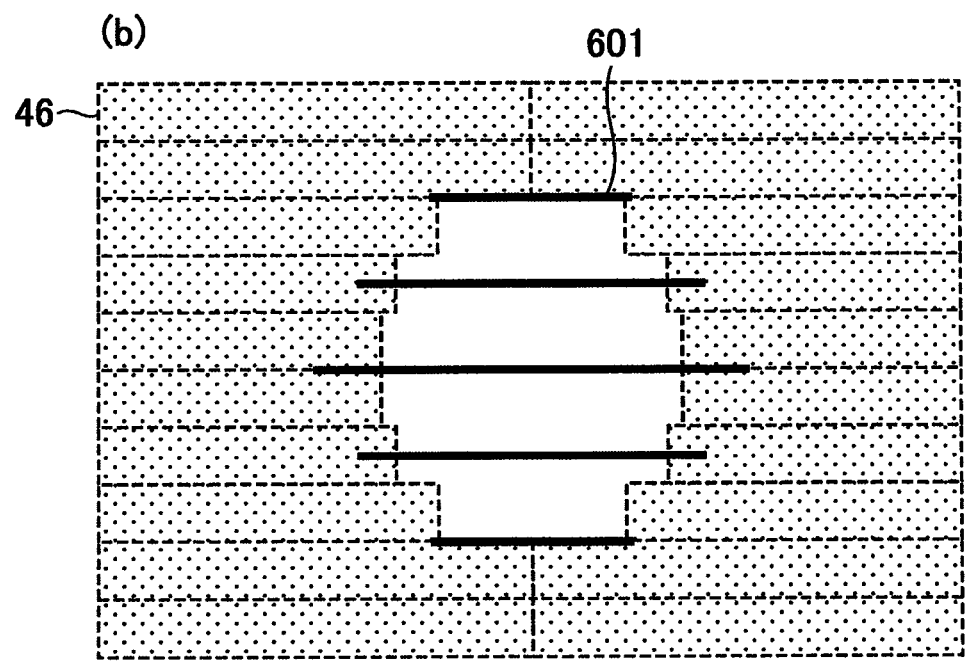
(b)

| | EXCITATION CURRENT VALUE X (A) | EXCITATION CURRENT VALUE Y (A) | BEAM CONTROL SIGNAL |
|---|---|---|---|
| 1 | 480 | −480 | ON |
| 2 | 480 | −420 | OFF |
| 3 | −480 | −420 | ON |
| 4 | −480 | −360 | OFF |
| ⋮ | ⋮ | ⋮ | |

TREATMENT PLANNING APPARATUS AND PARTICLE THERAPY SYSTEM

BACKGROUND OF THE INVENTION

1. Field of the Invention

The present invention relates to a particle therapy system for conducting cancer treatment by irradiating tumor volumes with a charged particle beam accelerated by a particle accelerator, and a particle therapy planning apparatus (treatment planning apparatus for particle therapy) for arranging a treatment plan for particle therapy.

2. Description of the Related Art

A particle beam cancer treatment system is a system for conducting cancer treatment by irradiating tumor volumes with a charged particle beam accelerated by a particle accelerator. The charged particle beam is accelerated up to approximately the light speed by a particle accelerator such as a synchrotron accelerator or a cyclotron accelerator and transported to an irradiation nozzle by a beam transport system. The charged particle beam is shaped in the irradiation nozzle to form an irradiation field that is conformal to (i.e., that fits) the shape of the target volume and the shaped charged particle beam is applied to the patient. Methods for shaping the charged particle beam in the irradiation nozzle into the irradiation field include a scatterer irradiation method, a scanning irradiation method, etc. In the scatterer irradiation method, the charged particle beam is enlarged by a scatterer and a necessary part of the enlarged beam is cut out by a collimator and applied to the target volume. In the scanning irradiation method, the charged particle beam transported to the irradiation nozzle by the beam transport system is applied to the target volume while directly scanning the beam with scanning magnets so that the scanned beam fits the target shape. The scanning irradiation method is capable of forming a dose distribution coinciding with the target shape since a thin charged particle beam accelerated by the particle accelerator and transported by the beam transport system is directly scanned by the scanning magnets during the irradiation of the target volume, As an irradiation method placed between the scatterer irradiation method and the scanning irradiation method, there exists a method called "uniform scanning" as described in V. A. Anferov, "Scan pattern optimization for uniform proton beam scanning", Med. Phys. 36 (2009) 3560-3567 (hereinafter referred to as "Non-patent Literature 1") and S. Yonai, et al., "Evaluation of beam wobbling methods for heavy-ion radiotherapy", Med. Phys. 35 (2008) 927-938 (hereinafter referred to as "Non-patent Literature 2"). The uniform scanning is an irradiation method in which the charged particle beam enlarged by the scatterer is scanned by the scanning magnets during the irradiation so as to form a dose distribution that is uniform in lateral directions. In the uniform scanning, a ridge filter is used for enlarging the dose distribution in the depth direction, that is, for forming an SOBP (Spread Out Bragg Peak). Alternatively, the target volume is partitioned into a lot of layers, the layer to be irradiated is switched by changing the energy of the charged particle beam, and the SOBP is formed by properly adjusting the charged particle beam irradiation amount of each layer so that the dose distribution in the depth direction becomes uniform. In the uniform scanning, a bolus, as a patient-specific device for adjusting the dose distribution to the shape of the under surface of the target volume, may also be used. In order to determine the irradiation field shape in the lateral directions conformal to the target shape in the uniform scanning, a multi-leaf collimator (which automatically shapes the irradiation field) or a patient-specific collimator (prepared by cutting a metal plate to form an aperture in a shape conformal to the target volume by electrical discharge machining, etc.) is used.

While only one collimator aperture shape is used in the uniform scanning, there exists an irradiation method called "conformal layer stacking irradiation" in which the target volume is partitioned into layers and each of the layers is successively irradiated by adjusting the aperture of the multi-leaf collimator to the irradiation field shape of each layer, as described in T. Kanai, et al., "Commissioning of a conformal irradiation system for heavy-ion radiotherapy using a layer-stacking method", Med. Phys. 33 (2006) 2989-2997 (hereinafter referred to as "Non-patent Literature 3"). In the conformal layer stacking irradiation, the target volume is partitioned into a lot of layers and each of the layers is successively irradiated while scanning the charged particle beam with the scanning magnets so that the lateral dose distribution (dose distribution in the lateral directions) becomes uniform similarly to the uniform scanning. The conformal layer stacking irradiation is capable of forming a dose distribution conformal to the target shape since the dose distribution is adjusted to the shape of the under surface of the target volume by using the bolus (patient-specific device) and then each layer of the target volume is irradiated by adjusting the irradiation field shape in the lateral directions to the lateral shape of the layer by using the multi-leaf collimator. The conformal layer stacking irradiation automatically changes the irradiation field shape from layer to layer by employing the multi-leaf collimator for specifying the irradiation field shape in the lateral directions for the irradiation of each layer. In the conformal layer stacking irradiation, each layer of the layer-partitioned target volume is irradiated with a charged particle beam of constant energy, and the layer to be irradiated is switched by changing the energy of the charged particle beam. The conformal layer stacking irradiation is capable of forming a dose distribution more coinciding with the target shape compared to the scatterer irradiation method and the uniform scanning.

In either the uniform scanning or the conformal layer stacking irradiation, the lateral scan is conducted by scanning the charged particle beam, which has been enlarged by the scatterer, in the lateral directions as explained above. A charged particle beam having a larger beam size compared to that in the scanning irradiation method is scanned in the uniform scanning and the conformal layer stacking irradiation, and thus the irradiation field has to be formed by using a collimator so that the irradiation field shape in the lateral directions fits the target shape. In the uniform scanning, the patient-specific collimator prepared by electrical discharge machining or the multi-leaf collimator automatically shaping its aperture to fit the target shape is used. In the conformal layer stacking irradiation, the multi-leaf collimator is used since the collimator aperture has to be changed for each layer of the layer-partitioned target volume.

In the uniform scanning and the conformal layer stacking irradiation, in order to form a dose distribution uniform in the lateral directions orthogonal to the charged particle beam's propagation direction, the charged particle beam is enlarged with the scatterer and the beam having a larger beam size than in the scanning irradiation method is applied to the target shape while scanning the beam in the lateral directions, as described in the Non-patent Literatures 1-3, Japanese Patent No. 3518270 (hereinafter referred to as "Patent Literature 1"), and M. Komori, et al., "Optimization of Spiral-Wobbler System for Heavy-Ion Radiotherapy", Jpn. J. Appl. Phys. 43 (2004) 6463-6467 (hereinafter referred to as "Non-patent Literature 4"). As shown in the Patent Literature 1 and the Non-patent Literatures 1-4, there exist various methods for forming the uniform dose distribution by superposing a plurality of dose distributions having the Gaussian distribution shape during the scanning of the charged particle beam having the large beam size by use of the scanning magnets.

In the raster scan shown in the Non-patent Literature 1, the charged particle beam is scanned along a scan path in a rectangular area continuously like the one-stroke drawing (drawing a picture with one stroke of the brush) without turning the beam ON or OFF by the accelerator. An area with a uniform dose distribution can be formed by setting the scan line interval of the raster scan at less than $2\sigma$ with respect to the beam size $\sigma$ of the charged particle beam.

In the zigzag scan shown in the Non-patent Literature 2, scan velocities of the charged particle beam in the X and Y directions in the X-Y plane are set independently, and the beam is scanned in a zigzag shape continuously like the one-stroke drawing without turning the beam ON or OFF similarly to the raster scan. In the zigzag scan, an area with a uniform dose distribution can be formed by setting the interval between the scan lines constituting the zigzag shape at less than $2\sigma$ ($\sigma$: beam size) similarly to the case of the raster scan.

In the circular wobbling shown in the Non-patent Literature 3, the charged particle beam is scanned along a circular scan path, continuously without turning the beam ON or OFF similarly to the raster scan and the zigzag scan. An area with a uniform dose distribution is formed around the center of the circular scan path.

In the spiral wobbling shown in the Non-patent Literature 4, the charged particle beam is scanned along a scan path in a spiral shape continuously without turning the beam ON or OFF. Similarly to the circular wobbling, an area with a uniform dose distribution is formed around the center of the spiral scan path.

In the line scan shown in the Patent Literature 1, the raster scan is combined with the ON/OFF control of the charged particle beam by the accelerator. Specifically, during the raster scan in the X-Y plane, the beam is kept ON in the X-direction scans so as to continuously irradiate the target volume and is kept OFF in the Y-direction scans so as not to irradiate the target volume. In the line scan, an area with a uniform dose distribution is formed by superposing a plurality of continuous X-direction linear dose distributions (like lines extending in the X direction) in the Y direction.

Among the above scanning methods, the raster scan, the zigzag scan, the spiral wobbling and the line scan (in which the beam size of the charged particle beam enlarged by the scatterer is smaller than in the circular wobbling) have some advantages over the circular wobbling, in that the thickness of the scatterer can be decreased, the energy loss of the charged particle beam in the scatterer can be reduced, and consequently, a longer reachable range of the charged particle beam can be achieved. Further, thanks to the small beam size of the charged particle beam, higher beam utilization efficiency can be achieved compared to the circular wobbling. On the other hand, due to the small beam size of the charged particle beam, the scan path tends to be longer than in the circular wobbling and the planar scan time necessary for forming the dose distribution uniform in the lateral directions tends to be longer.

SUMMARY OF THE INVENTION

In the uniform scanning, the irradiation of the target volume is conducted by using a beam scan path in the lateral directions corresponding to the irradiation field size which is determined by the size of the target volume. Thus, parts outside the collimator aperture area are also irradiated by the charged particle beam in areas where the collimator aperture area comes inward compared to the irradiation field size. Consequently, the time necessary for the irradiation tends to be long due to the beam scan path longer than necessary. Further, the amount of loss of the charged particle beam is large due to the irradiation of the parts outside the collimator aperture area.

In the conformal layer stacking irradiation, the beam scan in conventional techniques is conducted according to the same scan path for all the layers from the most distal (deepest) layer to the most proximal (shallowest) layer. Thus, even when the multi-leaf collimator is relatively closed to form a small aperture for the irradiation of the most proximal layer in the conformal layer stacking irradiation, the scanning of the charged particle beam for the layer is conducted using the same scan path as that for the most distal layer. Therefore, even when the projected shape of the target volume becomes smaller in proximal layers and the multi-leaf collimator aperture becomes smaller for the proximal layers, the irradiation is carried out also for the parts outside the aperture area. Consequently, the time necessary for the irradiation tends to be longer than necessary in the proximal layers. Further, the amount of loss of the charged particle beam is large due to the irradiation of the parts outside the multi-leaf collimator aperture area in the irradiation of the proximal layers.

It is therefore the primary object of the present invention to provide a treatment planning apparatus and a particle therapy system capable of shortening the charged particle beam scan path, reducing the treatment time, and decreasing the loss of the charged particle beam in the uniform scanning and the conformal layer stacking irradiation.

In the present invention, a treatment planning apparatus determines the charged particle beam scan path in the lateral directions in the uniform scanning as an optimum scan path for minimizing the irradiation of the parts other than the collimator aperture area, in consideration of the shape of the collimator aperture. Further, in cases where each layer of the layer-partitioned target volume is irradiated and scanned uniformly in the lateral directions in the conformal layer stacking irradiation, the present invention focuses on the fact that the multi-leaf collimator aperture area is the largest in the most distal (deepest) layer and gradually becomes smaller in more proximal (shallower) layers. When the multi-leaf collimator aperture area becomes smaller for the irradiation of a more proximal layer, the scan path is changed so that only the aperture area can be irradiated uniformly. In cases where each layer is irradiated and scanned in the lateral directions by means of the circular wobbling, for example, if the multi-leaf collimator aperture area becomes smaller in a more proximal layer, the wobbling radius of the circular wobbling is reduced so that only the smaller aperture area can be irradiated uniformly.

The treatment planning apparatus in the uniform scanning calculates the collimator aperture shape by searching the inside of the target volume based on X-ray CT (Computed Tomography) images. Thereafter, the treatment planning apparatus calculates a charged particle beam scan path for irradiating only the collimator aperture area with a uniform dose distribution. The treatment planning apparatus in the conformal layer stacking irradiation partitions the target volume into layers based on X-ray CT images and calculates the multi-leaf collimator aperture for the irradiation of each layer. Thereafter, the treatment planning apparatus calculates a minimum necessary scan path for uniformly irradiating only the multi-leaf collimator aperture area of each layer. As above, the treatment planning apparatus calculates a minimum scan path of the charged particle beam for uniformly irradiating only the collimator aperture area in consideration of the collimator aperture area (collimator aperture). As another means, it is possible in the conformal layer stacking irradiation to define an amount "irradiation field size of each layer" from the multi-leaf collimator aperture area regarding the irradiation of each layer of the layer-partitioned target volume. For example, when the multi-leaf collimator aperture area of a certain layer is contained in a circle of a 10 cm diameter, the irradiation field size of the layer is defined as 10 cm in diameter. An irradiation field size of a raster can also be defined. When the aperture area of a certain layer is contained in a 10 cm×10 cm square area, the irradiation field size of the layer is defined as 10 cm×10 cm. Data of a plurality of scan paths corresponding to various irradiation field sizes defined as above are held by a control apparatus of a particle therapy system as tables in a memory. The treatment planning apparatus calculates the irradiation field size of each layer. When the multi-leaf collimator aperture area is smaller (i.e., the irradiation field size is smaller) in a more proximal layer, the control apparatus selects a scan path corresponding to the small irradiation field size from the plurality of scan paths stored in the memory. By the addition of such a control apparatus, it becomes possible in the irradiation of each layer of the layer-partitioned target volume to scan the charged particle beam along the minimum scan path covering the lateral shape of each layer and thereby achieve a dose distribution uniform in the lateral directions.

With the means described above, it becomes possible in the uniform scanning to irradiate only the collimator aperture area with a uniform dose distribution while reducing the irradiation of parts other than the collimator aperture area. In the conformal layer stacking irradiation, it becomes possible to carry out the charged particle beam irradiation along the minimum irradiation path corresponding to the multi-leaf collimator aperture area of each layer. Consequently, in the uniform scanning, the scan path can be shortened compared to the conventional technique and the time necessary for the irradiation can be reduced. In the conformal layer stacking irradiation, the scan path can be shortened in proximal layers compared to the conventional technique and the time necessary for the irradiation can be reduced. In either the uniform scanning or the conformal layer stacking irradiation, the charged particle beam irradiation of the parts outside the collimator aperture area can be reduced.

According to the present invention, the charged particle beam scan path can be shortened and the treatment time can be reduced in the uniform scanning and the conformal layer stacking irradiation compared to the conventional techniques.

BRIEF DESCRIPTION OF THE DRAWINGS

FIG. 4A is a schematic diagram showing the shape of the most distal layer (layer 1) (viewed in the beam propagation direction) calculated by a treatment planning apparatus for the spherical target volume shown in FIG. 3 and the result of calculation of a multi-leaf collimator aperture for the shape of the layer 1.

FIG. 4B is a schematic diagram showing the shape of the sixth layer (layer 6) from the most distal layer (viewed in the beam propagation direction) calculated by the treatment planning apparatus for the spherical target volume shown in FIG. 3 and the result of calculation of the multi-leaf collimator aperture for the shape of the layer 6.

FIG. 12A is a schematic diagram showing the multi-leaf collimator aperture area for the most distal layer (layer 1) and a raster scan path according to the present invention determined for the spherical target volume shown in FIG. 3 by treatment planning for the conformal layer stacking irradiation.

FIG. 12B is a schematic diagram showing the multi-leaf collimator aperture area for the layer 6 situated at a more proximal (shallower) position and a raster scan path according to the present invention determined for the spherical target volume shown in FIG. 3 by treatment planning for the conformal layer stacking irradiation.

FIG. 13 is a table showing scanning magnet excitation current values in a case where the raster scan is conducted according to the present invention in the conformal layer stacking irradiation.

FIG. 15A is a schematic diagram showing the multi-leaf collimator aperture area for the most distal layer (layer 1) and a zigzag scan path according to the present invention determined for the spherical target volume shown in FIG. 3 by treatment planning for the conformal layer stacking irradiation.

FIG. 15B is a schematic diagram showing the multi-leaf collimator aperture area for the layer 6 situated at the more proximal (shallower) position and a zigzag scan path according to the present invention determined for the spherical target volume shown in FIG. 3 by treatment planning for the conformal layer stacking irradiation.

FIG. 16A is a schematic diagram showing the multi-leaf collimator aperture area for the most distal layer (layer 1) and a circular wobbling scan path according to the present invention determined for the spherical target volume shown in FIG. 3 by treatment planning for the conformal layer stacking irradiation.

FIG. 16B is a schematic diagram showing the multi-leaf collimator aperture area for the layer 6 situated at the more proximal (shallower) position and a circular wobbling scan path according to the present invention determined for the spherical target volume shown in FIG. 3 by treatment planning for the conformal layer stacking irradiation.

FIG. 17A is a schematic diagram showing the multi-leaf collimator aperture area for the most distal layer (layer 1) and a spiral wobbling scan path according to the present invention determined for the spherical target volume shown in FIG. 3 by treatment planning for the conformal layer stacking irradiation.

FIG. 17B is a schematic diagram showing the multi-leaf collimator aperture area for the layer 6 situated at the more proximal (shallower) position and a spiral wobbling scan path according to the present invention determined for the spherical target volume shown in FIG. 3 by treatment planning for the conformal layer stacking irradiation.

FIG. 18A is a schematic diagram showing the multi-leaf collimator aperture area for the most distal layer (layer 1) and a line scan path according to the present invention determined for the spherical target volume shown in FIG. 3 by treatment planning for the conformal layer stacking irradiation.

FIG. 18B is a schematic diagram showing the multi-leaf collimator aperture area for the layer 6 situated at the more proximal (shallower) position and a line scan path according to the present invention determined for the spherical target volume shown in FIG. 3 by treatment planning for the conformal layer stacking irradiation.

DESCRIPTION OF THE PREFERRED EMBODIMENTS

Figure 1:
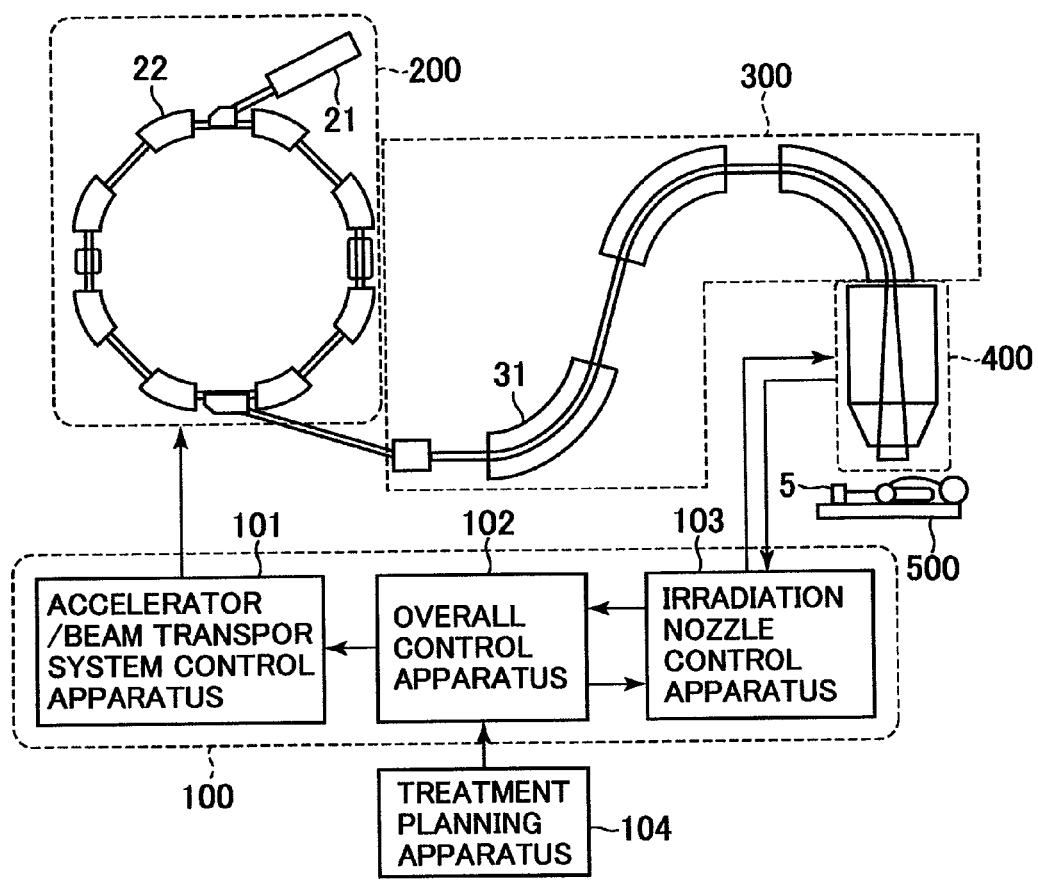
FIG. 1 is a schematic diagram showing the overall configuration of a particle therapy system and a control system pertinent to the present invention.

Referring now to the drawings, a description will be given in detail of preferred embodiments in accordance with the present invention.

FIG. 1 shows the overall configuration of a particle therapy system pertinent to the present invention. A charged particle beam is injected from an injector 21 into an accelerator 22 and is accelerated up to an intended energy. The charged particle beam accelerated by the particle accelerator 200 is transported to an irradiation nozzle 400 by a beam transport system 300 formed of a plurality of electromagnet arrays. The charged particle beam is shaped by the irradiation nozzle 400 to be conformal to (i.e., to fit) the shape of the target volume and then applied to the patient 5 lying on a bed apparatus 500. A treatment planning apparatus 104 arranges an irradiation plan for letting the doctor identify the target volume and irradiating the target volume with a uniform dose distribution, based on intra-body information on the patient (e.g., X-ray CT (Computed Tomography) image). Information on irradiation points, irradiation amount, etc. of the charged particle beam is transmitted from the treatment planning apparatus 104 to an overall control apparatus 102 of the particle therapy system. Based on the information, the overall control apparatus 102 carries out the irradiation while properly communicating information with an accelerator/beam transport system control apparatus 101 and an irradiation nozzle control apparatus 103.

Figure 2:
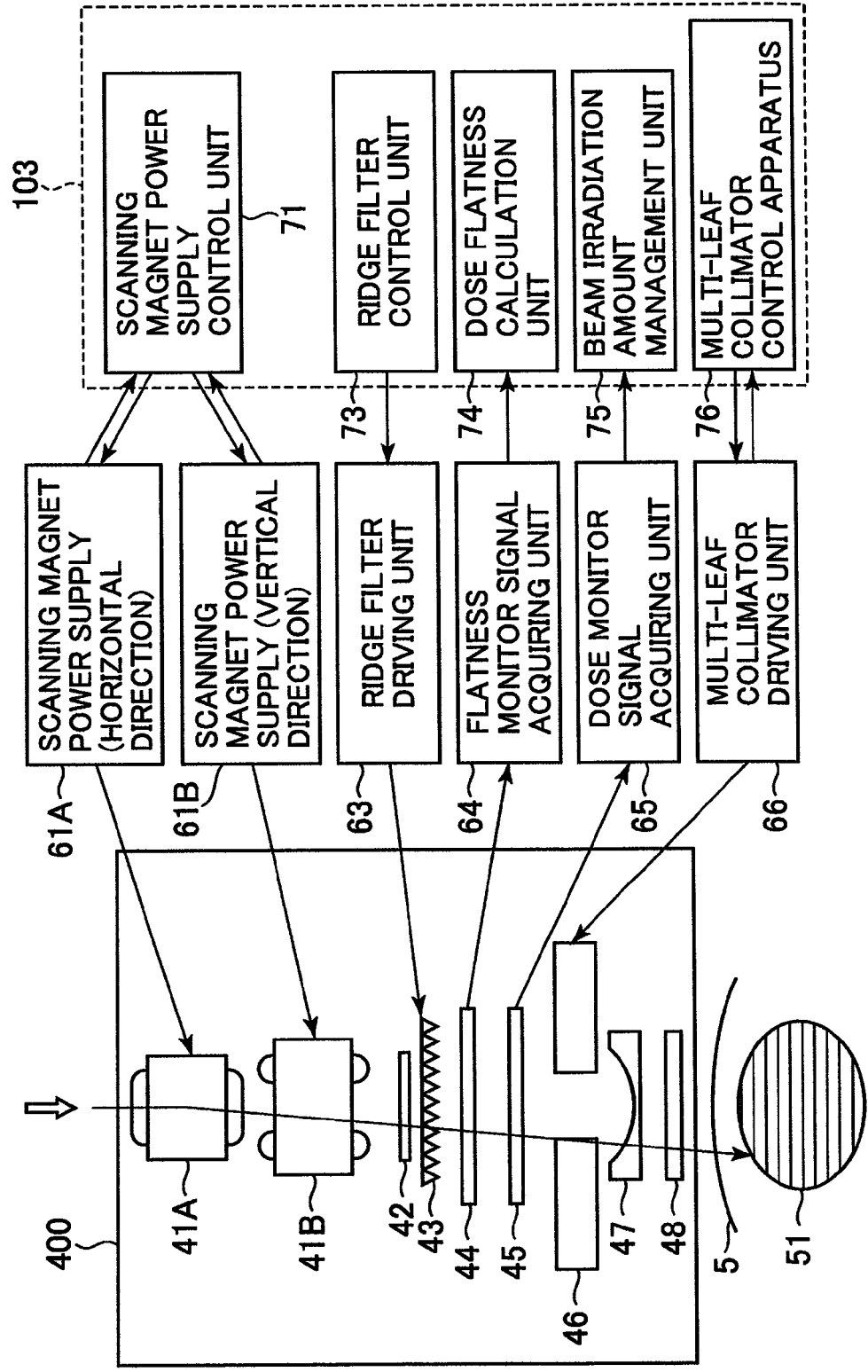
FIG. 2 is a schematic diagram showing an irradiation nozzle and its control apparatus pertinent to the present invention.

FIG. 2 shows the irradiation nozzle 400 and the irradiation nozzle control apparatus 103 pertinent to the present invention. Arranged in the irradiation nozzle 400 (from the upstream end) are a horizontal scanning magnet 41A and a vertical scanning magnet 41B for scanning the charged particle beam in lateral directions, a scatterer 42 for enlarging the beam size of the charged particle beam, a ridge filter 43 for enlarging the Bragg peak in the depth direction, a flatness monitor 44 for checking the uniformity of lateral dose distribution (dose distribution in the lateral directions) during the charged particle beam irradiation, a dose monitor 45 for measuring the irradiation amount of the charged particle beam, a multi-leaf collimator 46, a bolus 47 as a patient-specific device for adjusting the dose distribution in the depth direction to suit the shape of the under surface of the target volume, and a range shifter 48 for finely adjusting the reachable depth of the charged particle beam.

Figure 23:
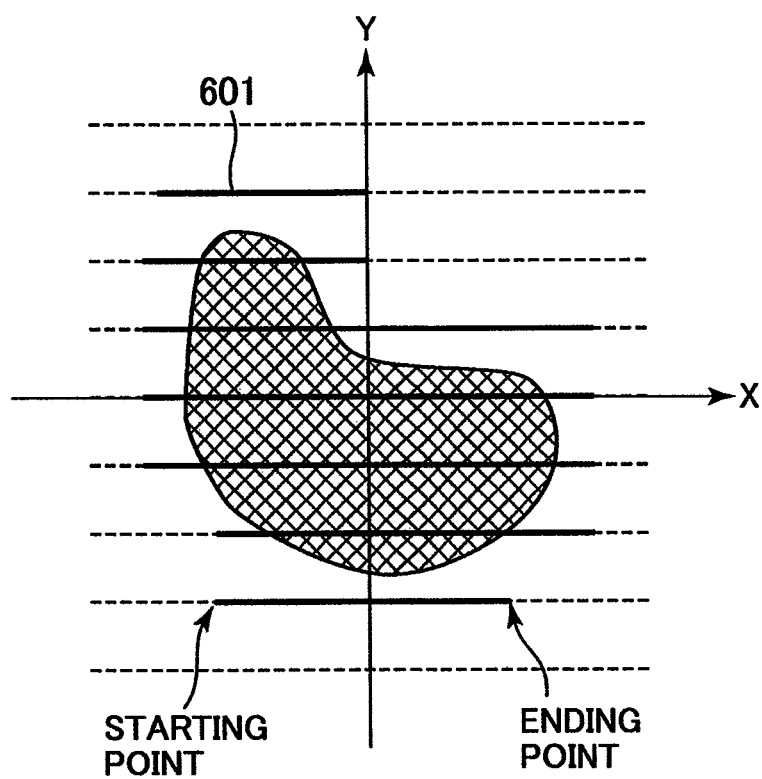
FIG. 23 is a schematic diagram showing the collimator aperture area and a line scan path in a case where the line scan is conducted according to the present invention in the uniform scanning.
Figure 24:
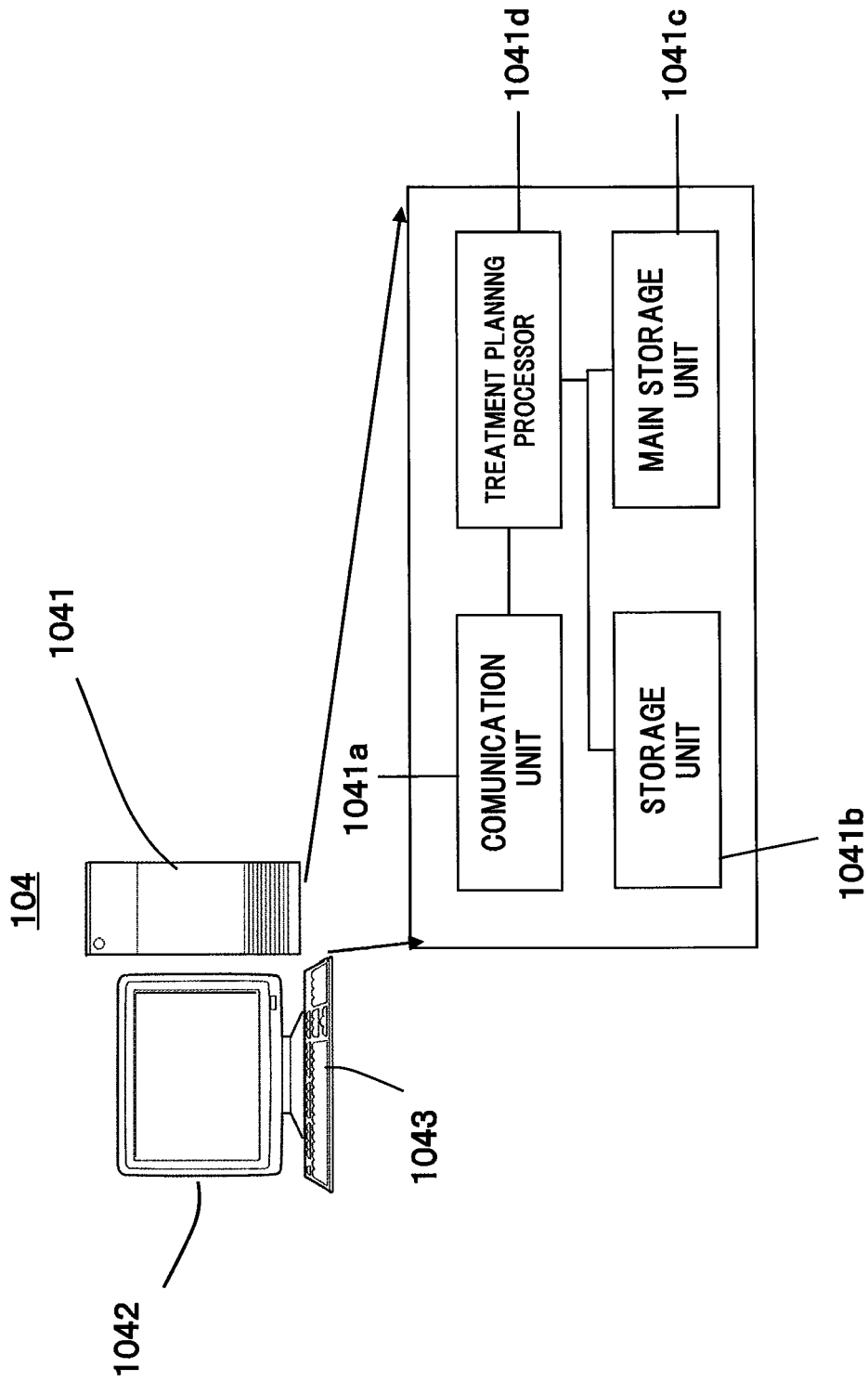
FIG. 24 is a schematic diagram showing the structure of the treatment planning apparatus.

FIG. 23 shows the structure of the treatment planning apparatus 104.

The treatment planning apparatus 104 comprises a treatment planning operation unit 1041, a monitor 1042 which displays X-ray CT images, MR images, dose distributions, etc., and an input device 1053 such as a keyboard, a mouse, or the like. The treatment planning operation unit 1041 is a device for managing storing of image data and dose distribution data for treatment planning, and includes a communication unit 1041a, a storage unit 1041b, a main storage unit 1041c and a treatment planning processor 1041e. The communication unit 1041a is used for data exchange through a new work with the other devices such as a database not shown, the overall control apparatus 102, X-ray CT, etc. The storage unit 1041b is a magnetic storage of high capacity, for example, and is used to store data in a long term and to store programs. The main storage unit 1041c is a RAN, for example, and mainly used to store data temporarily and the program executed. The treatment planning processor 1041e executes operational processing of the programs stored in the storage unit 1041b and the main storage unit 1041c.

Upon treatment planning, the treatment planning apparatus 104 executes various processes such as calculations, transmissions, etc explained below based on data input and instructions by an operator such as a doctor. At this time, the operator performs necessary data input and instructions by using the monitor 1042 and the input device 1053, and the treatment planning operation unit 1041 performs the processes such as calculations, transmissions, etc based on such data input and instructions by means of the communication unit 1041a, storage unit 1041b, main storage unit 1041c and treatment planning processor 1041e.

The flow of the treatment planning for the uniform scanning will be explained below.

The treatment planning apparatus 104 supporting the uniform scanning calculates the collimator aperture shape viewed in the irradiation direction of the charged particle beam by searching for points situated in the target volume 51 based on X-ray CT images. Further, the treatment planning apparatus 104 calculates the water-equivalent thickness of each point situated in the target volume 51 and thereby calculates a water-equivalent target volume thickness that is required for irradiating the target region with a uniform dose distribution in the depth direction (i.e., required SOBP length). In cases where the bolus is used for the uniform scanning, the treatment planning apparatus 104 also calculates the cutting shape of the bolus 47 based on the water-equivalent thickness of each point situated on the under surface of the target volume 51 so that the reachable position of the charged particle beam coincides with the under surface of the target volume. The collimator aperture shape can be provided with a margin as needed. Thereafter, the treatment planning apparatus 104 calculates a charged particle beam scan path for irradiating a collimator aperture area with a uniform dose distribution. Then, the treatment planning apparatus 104 performs a dose distribution calculation and thereby calculates the irradiation amount of the charged particle beam for irradiating the target volume with a uniform dose distribution. The collimator aperture shape, the SOBP length, the bolus shape, the charged particle beam scan path and the charged particle beam irradiation amount as the outputs of the treatment planning apparatus 104 are transmitted to the overall control apparatus 102 of the particle therapy system. In the uniform scanning, it is also possible to partition the target volume into layers, successively irradiate each layer with a charged particle beam of constant energy while changing the irradiation target layer by changing the energy of the charged particle beam, and form the uniform dose distribution in the depth direction of the target volume by properly setting the irradiation amount for each layer. In this case, data regarding the energy of the irradiating charged particle beam is also outputted from the treatment planning apparatus 104 to the overall control apparatus 102.

The irradiation procedure for the uniform scanning will be explained below.

Before the irradiation is started, data of the collimator aperture shape is sent from the overall control apparatus 102 to the irradiation nozzle control apparatus 103. In cases where a multi-leaf collimator is used for the uniform scanning, a multi-leaf collimator control apparatus 76 sends the aperture shape to a multi-leaf collimator driving unit 66, by which the multi-leaf collimator 46 is moved and set to form the aperture shape. In cases where a patient-specific collimator formed by the electrical discharge machining is used for the uniform scanning, the patient-specific collimator is previously cut (formed) in a prescribed shape and set at a prescribed position in the irradiation nozzle 400 before the irradiation. After completing the collimator setting, the multi-leaf collimator driving unit 66 sends a completion signal to the multi-leaf collimator control apparatus 76. In cases where the bolus is used, the bolus is cut according to the calculated cutting shape and set at a prescribed position in the irradiation nozzle 400 before the irradiation. The SOBP length is sent from the overall control apparatus 102 to a ridge filter control unit 73 in the irradiation nozzle control apparatus 103. The ridge filter control unit 73 selects a ridge filter 43 corresponding to the SOBP length and sends a signal to a ridge filter driving unit 63 to make the unit 63 set the selected ridge filter. After completing the setting of the ridge filter 43, the ridge filter driving unit 63 sends a setting completion signal to the ridge filter control unit 73. A scanning magnet power supply control unit 71 receives excitation current values at the starting point of the scanning from the overall control apparatus 102 and sends the excitation current values to scanning magnet power supplies 61A and 61B to instruct the power supplies 61A and 61B to make their settings. After completing the settings, the scanning magnet power supplies 61A and 61B send completion signals to the scanning magnet power supply control unit 71. Since the preparation for starting the irradiation is completed at this point, the overall control apparatus 102 sends a beam-on signal to the accelerator/beam transport system control apparatus 101 while sending a scan start signal to the scanning magnet power supply control unit 71 in the irradiation nozzle control apparatus 103, by which the irradiation is started.

The dose monitor 45 measures the electric charge of the charged particle beam irradiating the target volume. A beam irradiation amount management unit 75 in the irradiation nozzle control apparatus 103 outputs an irradiation completion signal when an irradiation amount determined by the treatment planning apparatus 104 is reached. The irradiation completion signal is sent from the irradiation nozzle control apparatus 103 to the overall control apparatus 102. Upon receiving the irradiation completion signal, the overall control apparatus 102 immediately sends a beam-off signal to the accelerator/beam transport system control apparatus 101, by which the irradiation is completed. During the irradiation, the flatness monitor 44 checks whether the lateral dose distribution (dose distribution in the lateral directions) is uniform or not. When deterioration of the flatness below a tolerance (permissible level) is detected, the information is sent from the flatness monitor 44 to the overall control apparatus 102, by which a beam-off process is executed immediately.

In the aforementioned case where the target volume is partitioned into a plurality of layers and each layer is successively scanned and irradiated with a charged particle beam of constant energy, when the irradiation of a layer is completed, data regarding the energy of the charged particle beam corresponding to the next layer is sent to the accelerator/beam transport system control apparatus 101, and the scanning magnet power supply control unit 71 sets the excitation current values of the scanning magnet power supplies 61A and 61B at those at the scan starting point. After the completion of the setting, the beam irradiation is restarted. When an irradiation amount for each layer determined by the treatment planning apparatus 104 is reached, the beam is stopped and the irradiation of the layer is finished. This procedure is repeated for all the layers. There are some methods for changing the energy of the charged particle beam. For example, the energy can be changed by controlling the accelerator, by inserting the range shifter arranged in the irradiation nozzle or the material called "degrader" arranged in the middle of the beam transport system by an appropriate amount during the passage of the beam, etc.

The flow of the treatment planning for the conformal layer stacking irradiation will be explained below.

The treatment planning apparatus 104 supporting the conformal layer stacking irradiation partitions the target volume into layers (each of which can be irradiated with a charged particle beam of constant energy) by calculating the water-equivalent thickness of each point situated in the target volume. By this process, the three-dimensional shape of each layer of the target volume is determined. The treatment planning apparatus 104 calculates the multi-leaf collimator aperture shape for each layer according to the shape of each layer viewed in the propagation direction of the charged particle beam. The treatment planning apparatus 104 also calculates an irradiation field size that covers the multi-leaf collimator aperture area of each layer. The irradiation field size is expressed in a rectangular shape (e.g., 10 cm square) or a circular shape (e.g., 10 cm diameter). The multi-leaf collimator aperture shape for each layer can be provided with a margin as needed. The treatment planning apparatus 104 calculates the scan path of the charged particle beam for irradiating the multi-leaf collimator aperture area of each layer with a uniform dose distribution. Thereafter, the treatment planning apparatus 104 executes the dose distribution calculation and thereby calculates the irradiation amount of the charged particle beam for each layer for irradiating the target volume with a uniform dose distribution. The charged particle beam scan path and the charged particle beam irradiation amount as the outputs of the treatment planning apparatus 104 are transmitted to the overall control apparatus 102 of the particle therapy system.

Figure 3:
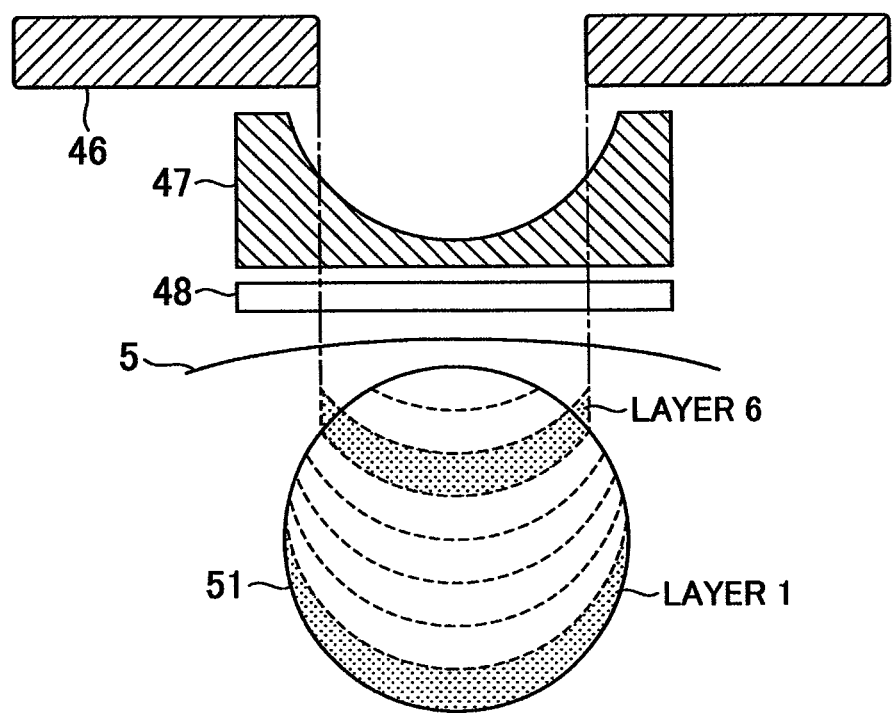
FIG. 3 is a schematic diagram showing irradiation of a spherical target volume by means of conformal layer stacking irradiation.
Figures 5, 6:
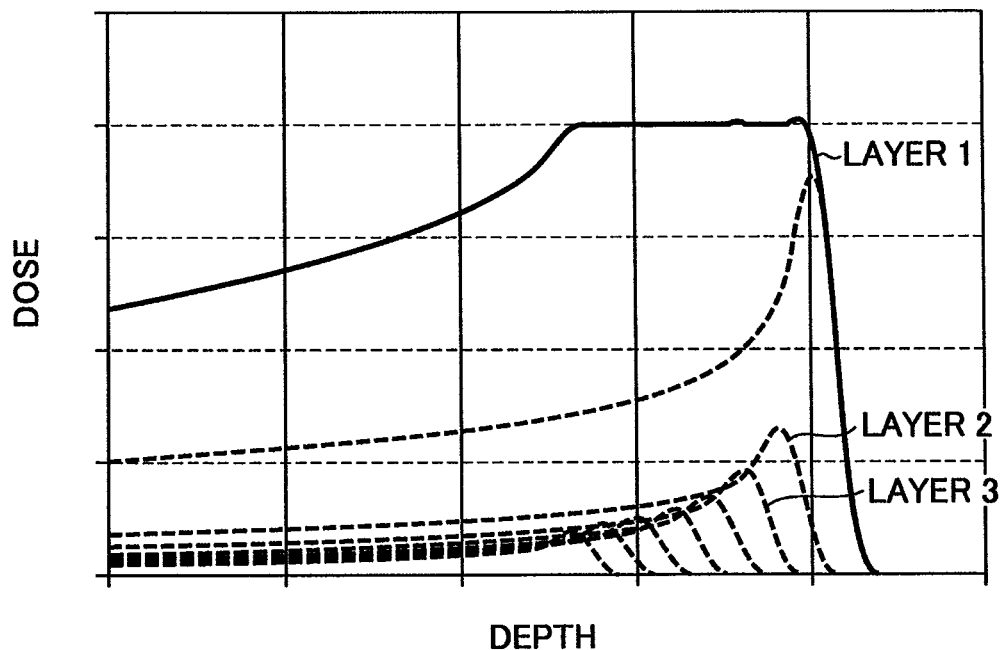
FIG. 5 is a graph showing formation of an SOBP in the conformal layer stacking irradiation achieved by the treatment planning apparatus by adjusting the irradiation amount for each layer so that the dose distribution in the depth direction becomes uniform.
FIG. 6 is a table showing the result of calculation of the irradiation amount for each layer executed by the treatment planning apparatus for achieving the uniform dose distribution in the depth direction in the conformal layer stacking irradiation.

The above operation of the treatment planning apparatus 104 for the conformal layer stacking irradiation will be explained more specifically referring to FIG. 3, by taking an example of conformal layer stacking irradiation of a target volume in a spherical shape. The treatment planning apparatus 104 calculates the cutting shape of the bolus 47 so that the reachable position of the charged particle beam coincides with the under surface of the target volume 51, by calculating the water-equivalent thickness of each point situated on the under surface of the spherical target volume 51. Further, by calculating the water-equivalent thickness of each point situated in the target volume 51, the treatment planning apparatus 104 partitions the target volume 51 into layers so that each layer can be irradiated with constant charged particle beam energy, and then calculates the charged particle beam energy for irradiating each layer or the level of insertion of the range shifter 48 for adjusting the reachable range to each layer. In the example of FIG. 3, the spherical target volume 51 is partitioned into a total of eight layers (layer 1-layer 8). The layer 1 represents the most distal (deepest) layer, and the positions of the layers become more proximal (shallower) with the increase in the layer number. The layer 6 represents the sixth layer from the most distal layer. The treatment planning apparatus 104 calculates the aperture shape of the multi-leaf collimator 46 for each layer by searching for points situated in the same layer. FIGS. 4A and 4B show the shapes (in the lateral directions) of the most distal layer (layer 1) and the sixth layer (layer 6) from the most distal layer viewed in the beam propagation direction and the result of the calculation of the multi-leaf collimator aperture by the treatment planning apparatus 104. As shown in FIGS. 4A and 4B, the treatment planning apparatus determines the aperture area of the multi-leaf collimator 46 to be conformal to (i.e., to fit) the lateral shape of each layer. The aperture area of the multi-leaf collimator 46 can be provided with a proper margin according to designation by the treatment planning apparatus 104, and thus the multi-leaf collimator aperture can enlarge from that shown in FIG. 4 to have a margin compared to the shape of the target volume 51. Since the bolus is used in the conformal layer stacking irradiation, irradiation of the outermost periphery of the target volume viewed in the beam propagation direction is conducted in the irradiation of the most distal layer. Thus, the multi-leaf collimator aperture is the largest for the most distal layer and closes gradually for more proximal layers. As is clear from FIGS. 4A and 4B, comparing the layer 1 (most distal layer) and the layer 6, the multi-leaf collimator aperture for the layer 6 situated at a more proximal (shallower) position is smaller than that for the layer 1 since the projected shape of the layer 6 is smaller. After determining the multi-leaf collimator aperture for each layer, the treatment planning apparatus 104 calculates the scan path appropriate for irradiating the multi-leaf collimator aperture area with a uniform dose distribution of the charged particle beam. As will be described later, there are several types of scan paths for implementing the charged particle beam irradiation uniform in the lateral directions. Finally, the treatment planning apparatus 104 determines the irradiation amount of the charged particle beam for each layer for irradiating the layer-partitioned target volume with a uniform dose distribution. As shown in FIG. 5, a dose distribution SOBP (Spread Out Bragg Peak) uniform in the depth direction can be formed by appropriately determining the irradiation amount for each layer. FIG. 6 shows the result of the calculation of the irradiation amount for each layer (layer 1-layer 8) for irradiating the spherical body with a uniform dose distribution. The charged particle beam scan path and the charged particle beam irradiation amount for each layer as the outputs of the treatment planning apparatus 104 are sent to the overall control apparatus 102 of the particle therapy system. The information on the scan path for forming the dose distribution uniform in the lateral directions is converted into sequences of excitation current target values for the horizontal and vertical scanning magnets 41A and 41B and sent to the overall control apparatus 102. The excitation current target values are sent from the overall control apparatus 102 to the scanning magnet power supply control unit 71 in the irradiation nozzle control apparatus 103. The scanning magnet power supply control unit 71 sends excitation current values to the scanning magnet power supplies 61A and 61B.

The irradiation procedure for the conformal layer stacking irradiation will be explained below.

First, before the irradiation of a layer is started, information on of the aperture shape of the multi-leaf collimator 46 is sent from the overall control apparatus 102 to the multi-leaf collimator control apparatus 76. Based on the information, the multi-leaf collimator driving unit 66 moves the multi-leaf collimator 46 to form the aperture shape. After completing the setting, the multi-leaf collimator driving unit 66 sends the completion signal to the multi-leaf collimator control apparatus 76. The scanning magnet power supply control unit 71 receives the excitation current values at the starting point of the scanning from the overall control apparatus 102 and sends the excitation current values to the scanning magnet power supplies 61A and 61B to instruct the power supplies 61A and 61B to make their settings. After completing the settings, the scanning magnet power supplies 61A and 61B send the completion signals to the scanning magnet power supply control unit 71. Since the preparation for starting the irradiation of a layer is completed at this point, the overall control apparatus 102 sends the beam-on signal to the accelerator/beam transport system control apparatus 101 while sending the scan start signal to the scanning magnet power supply control unit 71 in the irradiation nozzle control apparatus 103, by which the irradiation of a layer is started.

The dose monitor 45 measures the electric charge of the irradiating charged particle beam during the irradiation of a layer. The beam irradiation amount management unit 75 in the irradiation nozzle control apparatus 103 outputs an irradiation completion signal regarding the layer when an irradiation amount determined by the treatment planning apparatus 104 is reached. The irradiation completion signal is sent from the irradiation nozzle control apparatus 103 to the overall control apparatus 102. Upon receiving the irradiation completion signal, the overall control apparatus 102 immediately sends a beam-off signal to the accelerator/beam transport system control apparatus 101, by which the irradiation of the layer is completed. During the irradiation of a layer, the flatness monitor 44 checks whether the lateral dose distribution is uniform or not. When deterioration of the flatness below a tolerance (permissible level) is detected, the information is sent from the flatness monitor 44 to the overall control apparatus 102, by which the beam-off process is executed immediately.

After the irradiation of a layer is completed, the process advances to the preparation for the irradiation of the next layer. The overall control apparatus 102 sends information on the charged particle beam energy corresponding to the next layer to the accelerator/beam transport system control apparatus 101, while sending the multi-leaf collimator aperture shape corresponding to the next layer to the multi-leaf collimator control apparatus 76. Further, as mentioned above, the scanning magnet power supply control unit 71 sets the excitation current values of the scanning magnet power supplies 61A and 61B at the scan starting point. The energy of the charged particle beam can be changed by controlling the accelerator, by inserting the range shifter arranged in the irradiation nozzle or the material called "degrader" arranged in the middle of the beam transport system by an appropriate amount during the passage of the beam, etc.

In the uniform scanning, the irradiation is conducted while scanning the charged particle beam (enlarged by the scatterer 42) by use of the scanning magnets 41A and 41B so that the lateral dose distribution becomes uniform (as a result of the overlapping dose distributions each having the Gaussian distribution shape). In the conformal layer stacking irradiation, each layer of the layer-partitioned target volume 51 is irradiated with a charged particle beam of constant energy while scanning the charged particle beam by use of the scanning magnets 41A and 41B so that the lateral dose distribution becomes uniform. Scanning methods for forming the dose distribution uniform in the lateral directions in the uniform scanning or the conformal layer stacking irradiation by using the scanning magnets 41A and 41B include the raster scan, the zigzag scan, the circular wobbling, the spiral wobbling, the line scan, etc.

The charged particle beam scan paths for achieving the irradiation with the dose distribution uniform in the lateral directions will be explained referring to FIGS. 7-11.

Figure 7:
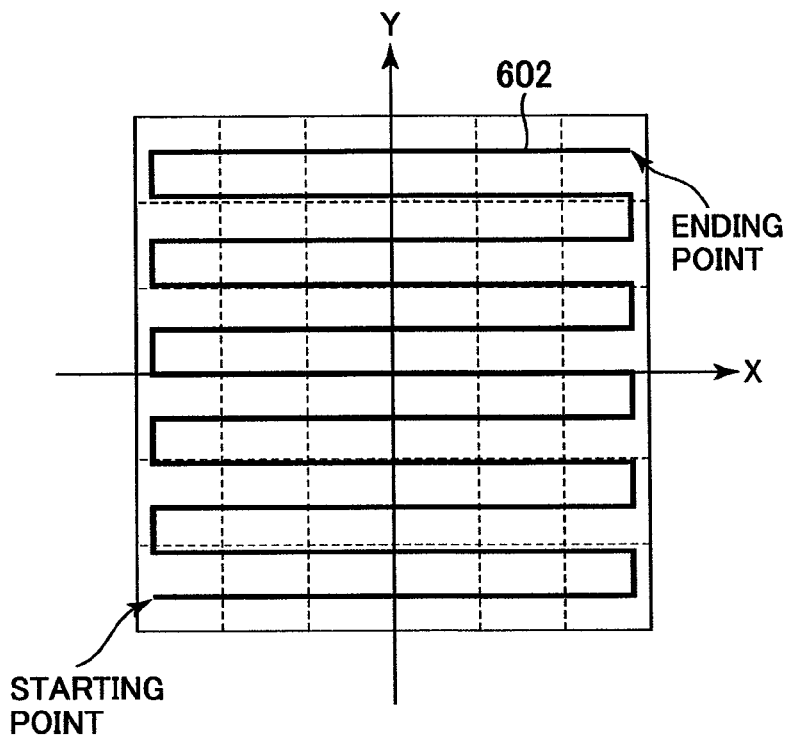
FIG. 7 is a schematic diagram showing a scan path in a case where each layer is laterally irradiated by means of the raster scan in the conformal layer stacking irradiation.

FIG. 7 shows a scan path 602 for the raster scan. In the raster scan, the beam is turned ON at the starting point shown in FIG. 7 and then the X-direction scan and the Y-direction scan are repeated until the beam reaches the ending point. The scan is continued from the starting point to the ending point like the one-stroke drawing (drawing a picture with one stroke of the brush) without turning the charged particle beam ON or OFF by the accelerator. Let "σ" represent the size of the charged particle beam, it is appropriate to set the Y-direction interval of the scan lines at less than 2σ. With this setting, a dose distribution uniform in the X-Y plane can be formed.

Figure 8:
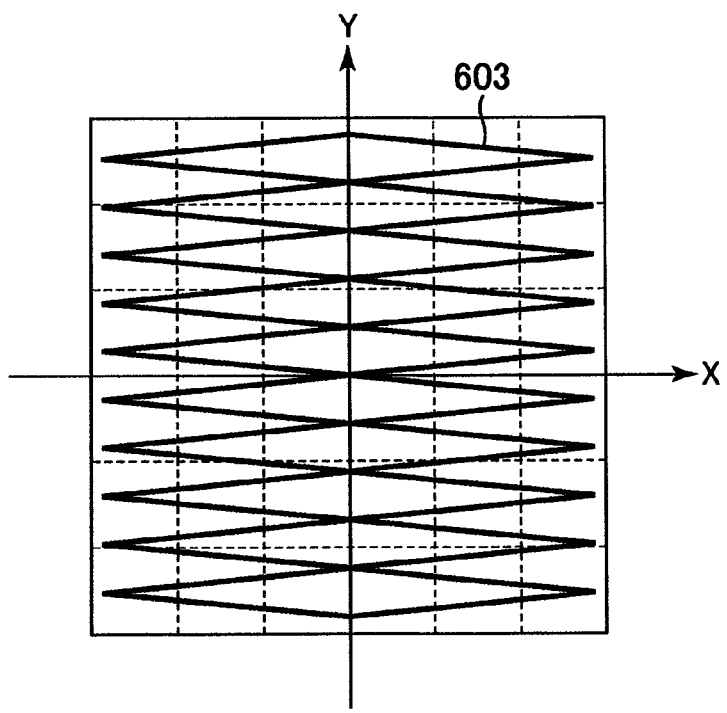
FIG. 8 is a schematic diagram showing a scan path in a case where each layer is laterally irradiated by means of the zigzag scan in the conformal layer stacking irradiation.

FIG. 8 shows a scan path 603 for the zigzag scan. In the zigzag scan, the beam is turned ON at the origin shown in FIG. 8 and the X-direction scan and the Y-direction scan are started simultaneously. Due to the X-direction scan and the Y-direction scan performed simultaneously, the scan path proceeds obliquely as shown in FIG. 8. When the beam reaches an ending point in the X direction or in the Y direction, the scanning direction is reversed. For example, when the beam during a scan in the +X direction reaches an ending point in the X direction, the scanning direction is reversed to the −X direction. The same goes for the Y direction. By properly selecting the scan velocities in the X and Y directions, the beam can be scanned to draw a zigzag scan path starting from the origin and returning to the origin as in FIG. 8. Also in the zigzag scan (similarly to the raster scan), the beam is scanned continuously from the origin to the origin like the one-stroke drawing without turning the beam OFF. Similarly to the case of the raster scan, a uniform dose distribution can be formed by setting the interval between the obliquely proceeding scan lines at less than 2σ with respect to the beam size σ.

Figure 9:
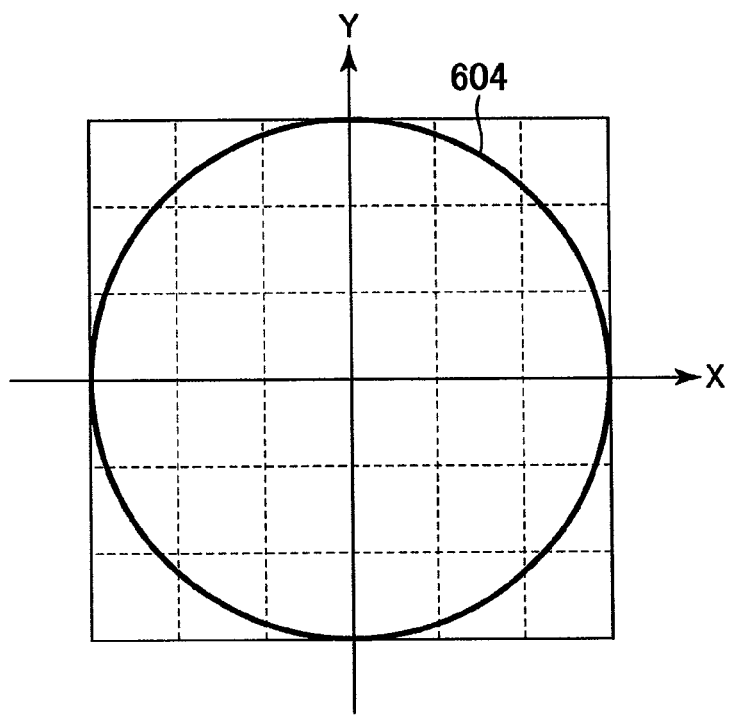
FIG. 9 is a schematic diagram showing a scan path in a case where each layer is laterally irradiated by means of the circular wobbling in the conformal layer stacking irradiation.

FIG. 9 shows a scan path 604 for the circular wobbling. In the circular wobbling, the beam is scanned continuously to draw a single circle, without turning the beam OFF. By properly selecting the radius of the scan circle and the beam size of the charged particle beam, a uniform dose distribution can be formed in the central part.

Figure 10:
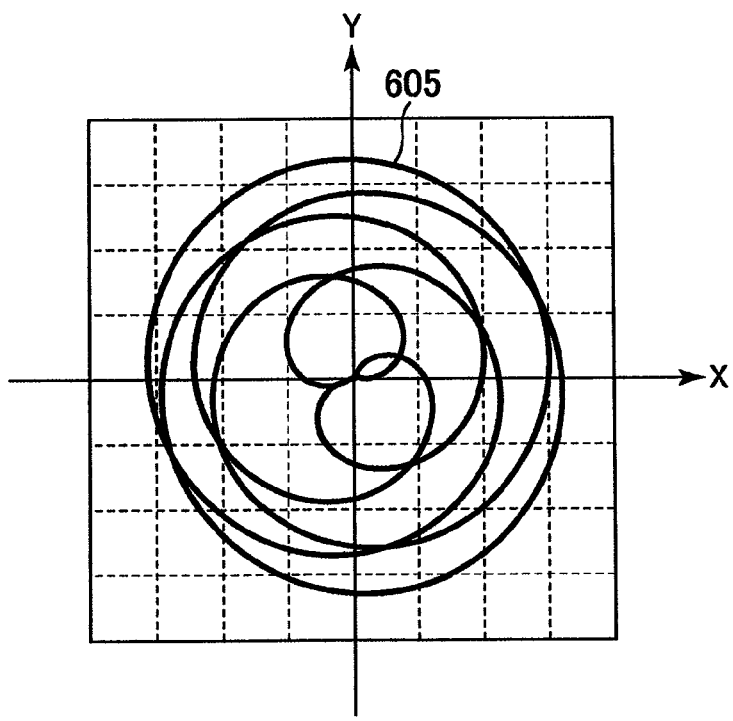
FIG. 10 is a schematic diagram showing a scan path in a case where each layer is laterally irradiated by means of the spiral wobbling in the conformal layer stacking irradiation.

FIG. 10 shows a scan path 605 for the spiral wobbling. In the spiral wobbling, a spiral starting from the origin and returning to the origin is repeated multiple times. Similarly to the circular wobbling, a uniform dose distribution is formed in the central part of the spiral wobbling.

Figure 11:
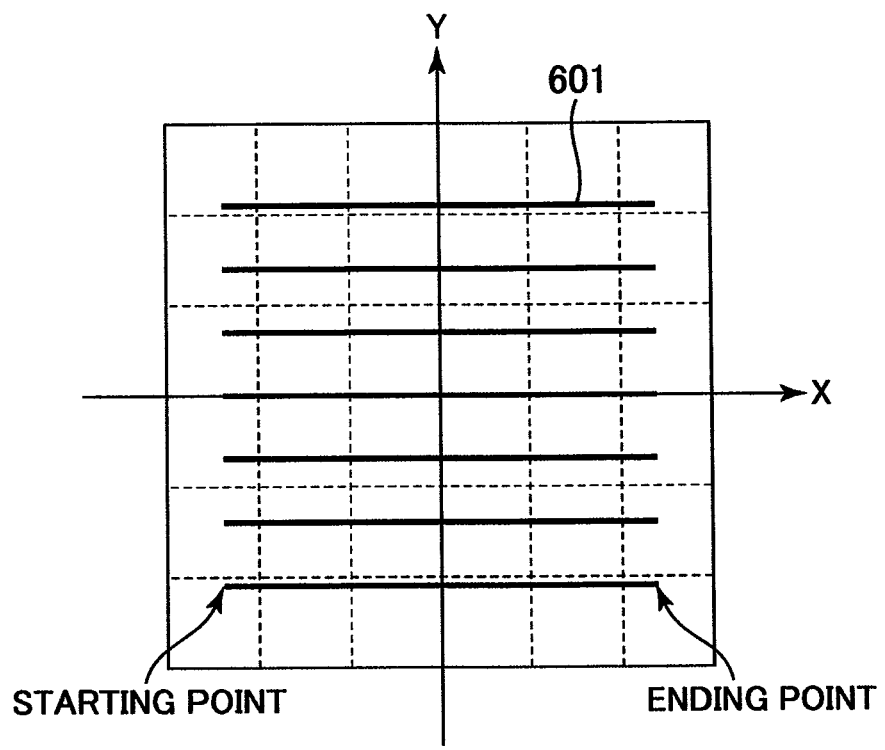
FIG. 11 is a schematic diagram showing a scan path in a case where each layer is laterally irradiated by means of the line scan in the conformal layer stacking irradiation.

FIG. 11 shows a scan path 601 for the line scan. In the line scan, the charged particle beam is turned ON at the starting point shown in FIG. 11, scanned in the X direction, and turned OFF at the ending point shown in FIG. 11. Thereafter, the irradiation point is moved in the Y direction and the beam scan in the X direction is repeated. As above, the line scan is conducted by performing each X-direction scan without turning the beam OFF and each Y-direction scan with the beam OFF, by which dose distributions like lines extending in the X direction are overlapped in the Y direction to form a uniform dose distribution. Similarly to the raster scan, a uniform dose distribution is formed by setting the Y-direction interval of the scan lines at less than 2σ with respect to the beam size σ.

For any of the scanning methods shown in FIGS. 7-11, the sequences of the excitation current values for the horizontal and vertical scanning magnets 41A and 41B corresponding to the scan path are previously stored as a table in a memory of the overall control apparatus 102 of the particle therapy system shown in FIG. 1. The excitation current values are sent to the scanning magnet power supply control unit 71 in the irradiation nozzle control apparatus 103 shown in FIG. 2. Meanwhile, the beam-on signal and the beam-off signal are properly sent from the overall control apparatus 102 to the accelerator/beam transport system control apparatus 101, by which the lateral irradiation according to the scan path (FIG. 7-FIG. 11) is carried out.

First Embodiment

Figures 19, 20:
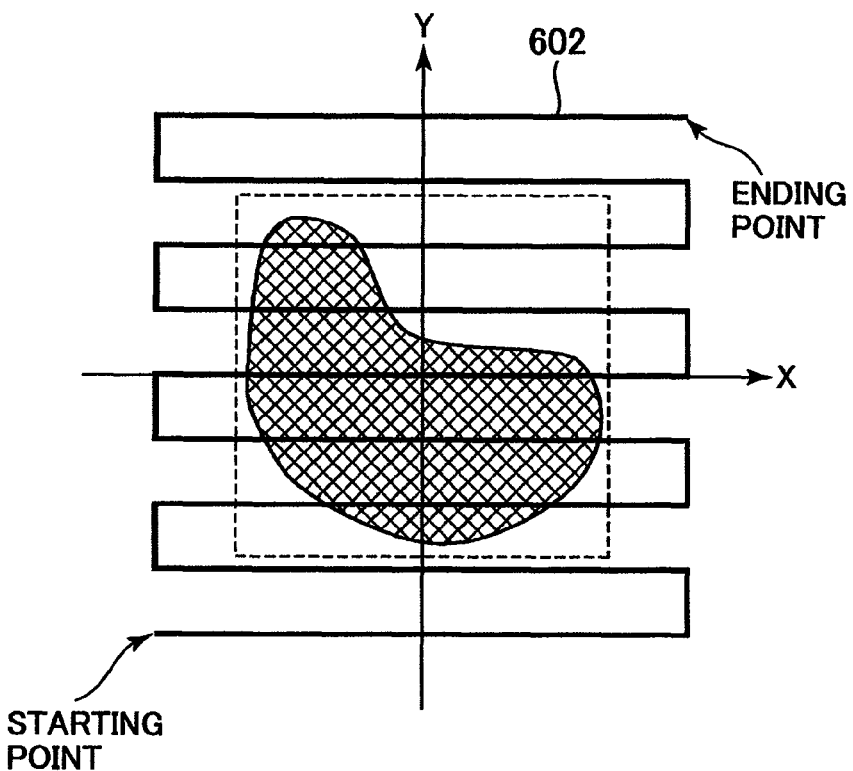
FIG. 19 is a table showing the scanning magnet excitation current values and beam ON/OFF control signals in a case where the line scan is conducted according to the present invention in the conformal layer stacking irradiation.
FIG. 20 is a schematic diagram showing the collimator aperture area and a conventional raster scan path in the uniform scanning.

A first embodiment as a preferred embodiment of the present invention relates to a case where the irradiation is conducted by performing the raster scan in the lateral directions in the uniform scanning. FIG. 20 shows a raster scan path in the conventional uniform scanning. In FIG. 20, the hatched area represents the collimator aperture area, the dotted line represents a rectangular irradiation field that covers the collimator aperture area, and the solid line represents the raster scan path 602. The raster scan is started at the starting point shown in FIG. 20, and the X-direction scan and the Y-direction scan are repeated without turning the beam OFF until the beam reaches the ending point shown in FIG. 20. In the conventional uniform scanning, the treatment planning apparatus determines an irradiation field that covers the collimator aperture area and calculates the raster scan path 602 for irradiating the irradiation field with a uniform dose distribution as shown in FIG. 20. Alternatively, the treatment planning apparatus 104 may previously calculate a plurality of raster scan paths corresponding to various irradiation fields and hold the calculated raster scan paths as data corresponding to the irradiation fields. In FIG. 20, for example, the treatment planning apparatus 104 sets the irradiation field size (rectangular area indicated by the dotted line) covering the target volume at 25 cm×25 cm, the beam size σ at approximately 2 cm, the scan interval in the Y direction at 4 cm (approximately twice the beam size), and the number of scan lines (counted in the Y direction) at 9. The scan range in the X direction is determined as a range from −18 cm to +18 cm, considering the formation of a uniform dose distribution by the irradiation of the irradiation field size (25 cm) in the X direction with a continuous beam and the drop in the dose distribution at both ends.

Figure 21:
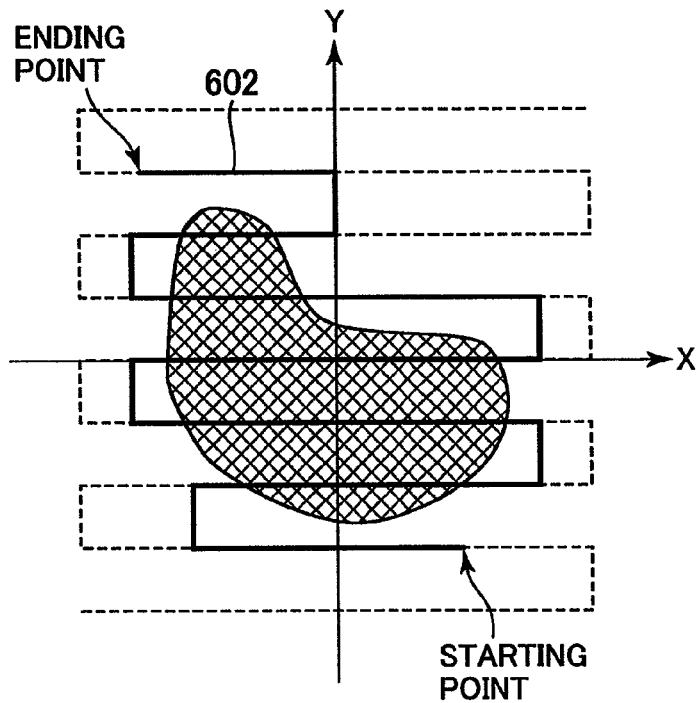
FIG. 21 is a schematic diagram showing the collimator aperture area and a raster scan path in a case where the raster scan is conducted according to the present invention in the uniform scanning.

FIG. 21 shows a raster scan path 602 that is set by the treatment planning apparatus 104 in accordance with the present invention. The hatched area represents the collimator aperture area similarly to FIG. 20. In FIG. 21, however, a raster scan path for irradiating only the collimator aperture area with a uniform dose distribution is shown. A method for calculating the raster scan path 602 that is employed by the treatment planning apparatus 104 in this embodiment will be explained below. First, the range of the collimator aperture area in the Y direction is determined. The beam size σ of the charged particle beam is determined as 2 cm, for example. The number of scan lines arranged in the Y direction is determined by setting the scan interval in the Y direction (see FIG. 7) as an element constituting the raster scan path. In the case of FIG. 21, for example, assuming that the range of the aperture area in the Y direction is a 20 cm range from −10 cm to +10 cm, the scan interval in the Y direction is set at 4 cm (approximately twice the beam size) and the number of scan lines is set at 7. The scan range in the X direction is determined for each scan line in the X direction so that the collimator aperture area can be irradiated with a uniform dose distribution, considering the drop in the dose distribution at both ends which varies depending on the beam size.

Information on the determined beam size is sent to the overall control apparatus 102 and the thickness of the scatterer is properly controlled by the nozzle control apparatus according to the beam size. FIG. 13 shows the sequences of the excitation current values corresponding to the scan path for the raster scan. The sequences in FIG. 13 are used for the two scanning magnets 41A and 41B shown in FIG. 2. The sequences shown in FIG. 13 are stored in the memory of the overall control apparatus 102 of the particle therapy system. The overall control apparatus 102 sends the excitation current values to the scanning magnet power supply control unit 71 successively from the top of the table, by which the scan in the lateral directions is carried out.

As explained above, the treatment planning apparatus 104 in this embodiment calculates the collimator aperture (collimator aperture area) for the irradiation of the target volume and thereafter calculates the optimum raster scan path 602 for irradiating only the collimator aperture area with a uniform dose distribution as shown in FIG. 21. As is clear from comparison between FIG. 20 and FIG. 21, parts of the scan path in FIG. 20 in the areas where the collimator aperture comes inward compared to the irradiation field size are left out in FIG. 21. This makes it possible to shorten the scan distance of the raster scan path 602 compared to the conventional technique and thereby reduce the treatment time. Further, the amount of the charged particle beam irradiating parts outside the collimator aperture area in the conventional technique can be reduced, by which the charged particle beam transported to the irradiation nozzle can be utilized with high efficiency.

Second Embodiment

Figure 22:
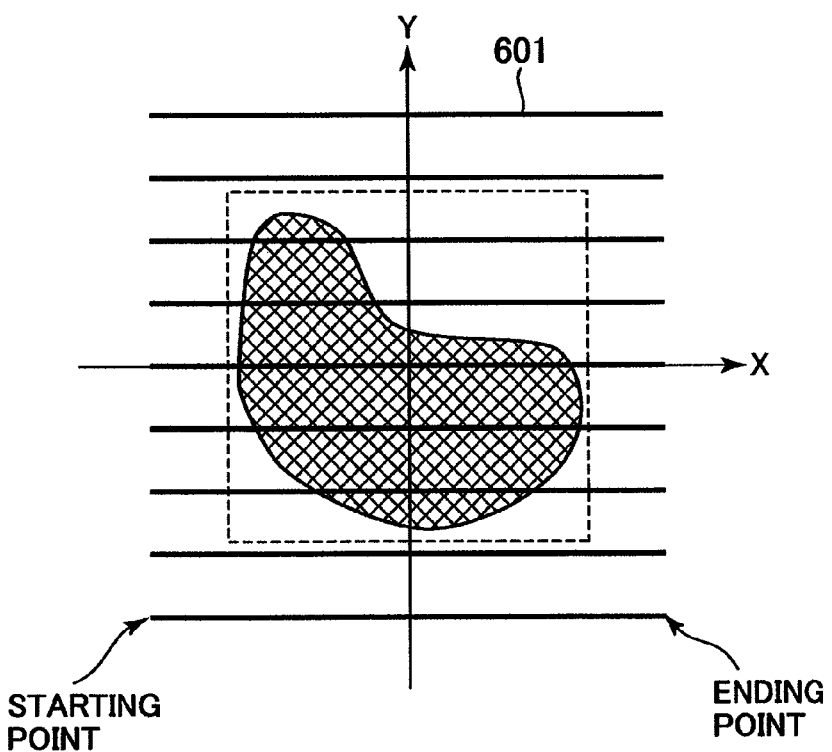
FIG. 22 is a schematic diagram showing the collimator aperture area and a conventional line scan path in the uniform scanning.

A second embodiment as another preferred embodiment of the present invention relates to a case where the irradiation is conducted by performing the line scan in the lateral directions in the uniform scanning. FIG. 22 shows a line scan path in the conventional uniform scanning. In FIG. 22, the hatched area represents the collimator aperture area, the dotted line represents a rectangular irradiation field that covers the collimator aperture area, and the solid lines represent the line scan path 601. The line scan is started in the X direction at the starting point shown in FIG. 22 and continued until the beam reaches the ending point shown in FIG. 22. This is a one-line irradiation in the line scan. The one-line irradiation is repeated in the Y direction, by which one planar scan is completed. In the conventional uniform scanning, the treatment planning apparatus 104 determines an irradiation field that covers the collimator aperture area and calculates the line scan path 601 for irradiating the irradiation field with a uniform dose distribution as shown in FIG. 22. Alternatively, the treatment planning apparatus 104 may previously calculate a line scan path corresponding to an irradiation field and hold the calculated line scan path as data corresponding to the irradiation field. In FIG. 22, for example, the treatment planning apparatus 104 sets the irradiation field size (rectangular area indicated by the dotted lines) covering the target volume at 25 cm×25 cm, the beam size σ at approximately 2 cm, the scan interval in the Y direction at 4 cm (approximately twice the beam size), and the number of scan lines arranged in the Y direction at 9. The scan range in the X direction is determined as a range from −18 cm to +18 cm, considering the formation of a uniform dose distribution by the irradiation of the irradiation field size (25 cm) in the X direction with a continuous beam and the drop in the dose distribution at both ends.

FIG. 23 shows a line scan path 601 that is set by the treatment planning apparatus 104 in accordance with the present invention. The hatched area represents the collimator aperture area similarly to FIG. 22. In FIG. 23, however, a line scan path 601 for irradiating only the collimator aperture area with a uniform dose distribution is shown. A method for calculating the line scan path 601 that is employed by the treatment planning apparatus 104 in this embodiment will be explained below. First, the range of the collimator aperture area in the Y direction is determined. The beam size σ of the charged particle beam is determined as 2 cm, for example. The number of scan lines arranged in the Y direction is determined by setting the scan interval in the Y direction as an element constituting the line scan path. In the case of FIG. 23, for example, assuming that the range of the aperture area in the Y direction is a 20 cm range from −10 cm to +10 cm, the scan interval in the Y direction is set at 4 cm (approximately twice the beam size) and the number of scan lines is set at 7. The scan range in the X direction is determined for each scan line so that only the collimator aperture area can be irradiated with a uniform dose distribution, considering the drop in the dose distribution at both ends which varies depending on the beam size.

Information on the determined beam size is sent to the overall control apparatus 102 and the thickness of the scatterer is properly controlled by the nozzle control apparatus according to the beam size. FIG. 19 shows the sequences of the excitation current values and beam control signals corresponding to the scan path for the line scan. The sequences in FIG. 19 are used for the two scanning magnets 41A and 41B shown in FIG. 2. The sequences shown in FIG. 19 are stored in the memory of the overall control apparatus 102 of the particle therapy system. The overall control apparatus 102 sends the excitation current values to the scanning magnet power supply control unit 71 successively from the top of the table, while turning the beam ON/OFF according to the beam control signals, by which the scan in the lateral directions is carried out.

As explained above, the treatment planning apparatus 104 in this embodiment calculates the collimator aperture (collimator aperture are) for the irradiation of the target volume and thereafter calculates the optimum line scan path 601 for irradiating only the collimator aperture area with a uniform dose distribution as shown in FIG. 22. Comparing FIG. 22 and FIG. 23, parts of the scan path in FIG. 22 in the areas where the collimator aperture comes inward compared to the irradiation field size are left out in FIG. 23. This makes it possible to shorten the scan distance of the line scan path 601 compared to the conventional technique and thereby reduce the treatment time. Further, the amount of the charged particle beam irradiating parts outside the collimator aperture area in the conventional technique can be reduced, by which the charged particle beam transported to the irradiation nozzle can be utilized with high efficiency.

Third Embodiment

A third embodiment as another preferred embodiment of the present invention relates to a case where each layer of the layer-partitioned target volume in the conformal layer stacking irradiation is irradiated and scanned in the lateral directions by means of the raster scan. In the conventional conformal layer stacking irradiation, every layer was irradiated using the raster scan path 602 shown in FIG. 7. FIG. 12A shows a raster scan path 602 for the most distal layer (layer 1) in this embodiment, and FIG. 12B shows a raster scan path 602 for the layer 6 situated at a more proximal (shallower) position. In FIGS. 12A and 12B, the raster scan path for the layer 6 is shortened compared to that for the layer 1 since the multi-leaf collimator aperture area is reduced. Each scan path shown in FIGS. 12A and 12B is calculated as the minimum scan path by the treatment planning apparatus 104 after calculating the multi-leaf collimator aperture for each layer of the layer-partitioned target volume.

A method for calculating the raster scan path 602 that is employed by the treatment planning apparatus 104 will be explained below. First, the ranges of the multi-leaf collimator aperture area in the X direction and in the Y direction are determined. The beam size σ of the charged particle beam is determined as 2 cm, for example. The number of scan lines arranged in the Y direction is determined by setting the scan interval in the Y direction (see FIG. 7) as an element constituting the raster scan path. For example, assuming that the range of the aperture area in the Y direction is a 10 cm range from −5 cm to +5 cm, the scan interval is set at 3.5 cm (less than twice the beam size) and the number of scan lines is set at 5. The scan range in the X direction is determined for each scan line in the X direction, considering the range of the aperture area in the X direction at the scan line and the drop in the dose distribution at both ends which varies depending on the beam size. The raster scan path is calculated and determined for each layer as above since the multi-leaf collimator aperture area varies from layer to layer.

Information on the determined beam size is sent to the overall control apparatus 102 and the thickness of the scatterer is properly controlled by the nozzle control apparatus according to the beam size. FIG. 13 shows the sequences of the excitation current values corresponding to the scan path for the raster scan. The sequences in FIG. 13 are used for the two scanning magnets 41A and 41B shown in FIG. 2. The sequences shown in FIG. 13 are stored in the memory of the overall control apparatus 102 of the particle therapy system. The overall control apparatus 102 sends the excitation current values to the scanning magnet power supply control unit 71 successively from the top of the table, by which the scan in the lateral directions is carried out.

As explained above, in the conformal layer stacking irradiation, the treatment planning apparatus 104 in this embodiment calculates the multi-leaf collimator aperture for each layer of the layer-partitioned target volume and thereafter calculates the minimum raster scan path for irradiating only the multi-leaf collimator aperture area of each layer with a uniform dose distribution. This shortens the scan length of the raster scan path for each layer compared to the conventional conformal layer stacking irradiation, by which the treatment time can be reduced. Further, the amount of the charged particle beam irradiating the closed area of the multi-leaf collimator in the conventional technique can be reduced, by which the charged particle beam transported to the irradiation nozzle can be utilized with high efficiency.

Fourth Embodiment

A fourth embodiment as another preferred embodiment of the present invention will be described referring to figures. The treatment planning apparatus 104 in the third embodiment calculated the scan path for each layer. In this embodiment, in the conformal layer stacking irradiation in which each layer of the layer-partitioned target volume is irradiated by means of the raster scan, a plurality of raster scan paths corresponding to various irradiation field sizes are prepared previously, and a scan path suitable for irradiating each layer is selected from the prepared raster scan paths.

The treatment planning apparatus 104 calculates the multi-leaf collimator aperture for each layer of the layer-partitioned target volume (i.e., the multi-leaf collimator aperture area of each layer). Subsequently, the treatment planning apparatus 104 calculates the minimum irradiation field size covering the aperture area. For example, an irradiation field size 10 cm×10 cm means that the multi-leaf collimator aperture area including the margin is contained in the 10 cm×10 cm area. As above, the treatment planning apparatus 104 calculates the irradiation field size of each layer of the layer-partitioned target volume in the conformal layer stacking irradiation.

Figure 14:
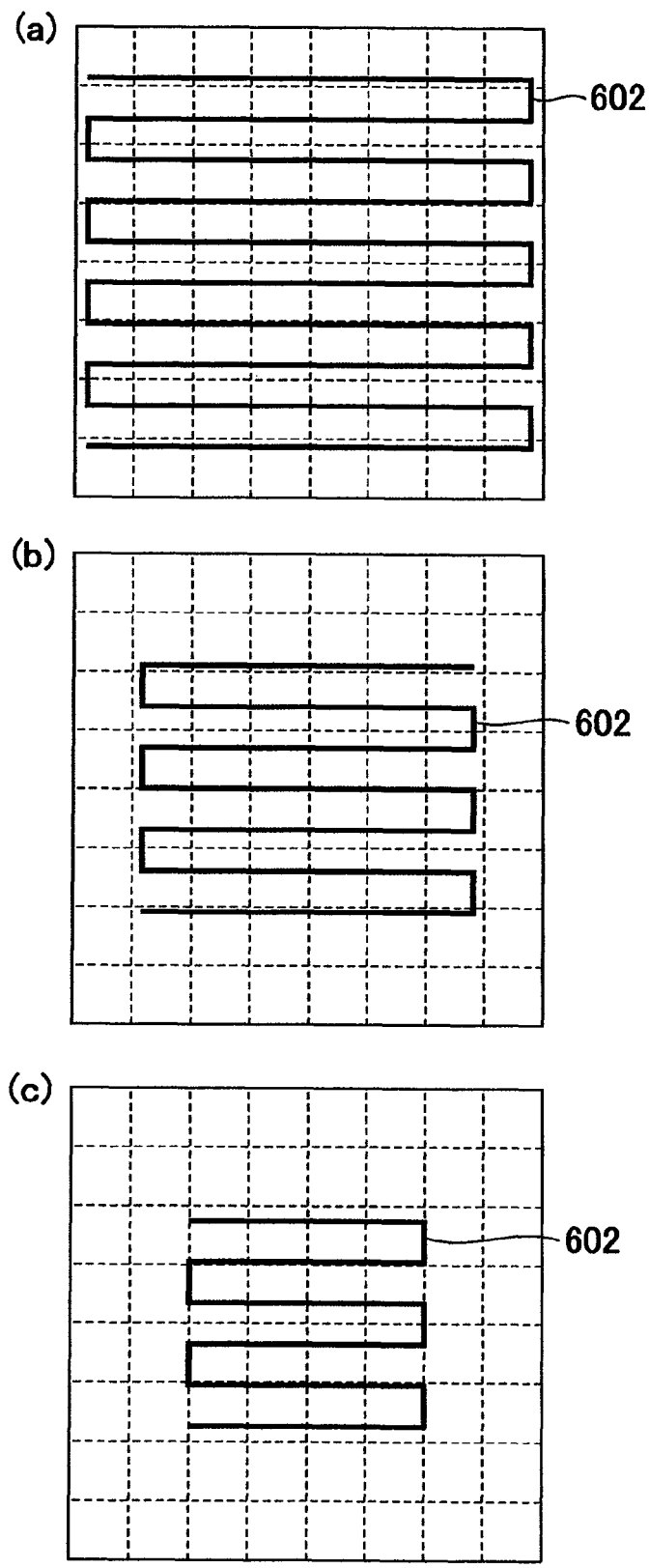
FIG. 14A is a schematic diagram showing a scan path corresponding to an irradiation field size 25 cm×25 cm in a case where the raster scan is used for the lateral irradiation in the conformal layer stacking irradiation.
FIG. 14B is a schematic diagram showing a scan path corresponding to an irradiation field size 15 cm×15 cm in the case where the raster scan is used for the lateral irradiation in the conformal layer stacking irradiation.
FIG. 14C is a schematic diagram showing a scan path corresponding to an irradiation field size 10 cm×10 cm in the case where the raster scan is used for the lateral irradiation in the conformal layer stacking irradiation.

On the other hand, a plurality of raster scan paths corresponding to various irradiation field sizes, allowing for the irradiation uniform in the lateral directions, are previously determined by calculation. FIGS. 14A, 14B and 14C show examples of the scan paths corresponding to various irradiation field sizes. FIGS. 14A, 14B and 14C show raster scan paths corresponding to irradiation field sizes 25 cm×25 cm, 15 cm×15 cm and 10 cm×10 cm, respectively. With the raster scan path 602 of FIG. 14A corresponding to the irradiation field size 25 cm×25 cm, a rectangular area of 25 cm×25 cm can be irradiated and scanned uniformly in the lateral directions. The method for determining the raster scan path corresponding to each irradiation field size is the same as that described in the first embodiment. Thus, the beam size, the scan line interval in the Y direction and the number of scan lines are determined and thereafter the raster scan path is determined so that the scan range in the X direction (irradiation field) can be irradiated uniformly. While only three types of scan paths corresponding to three irradiation field sizes are shown in FIG. 14, a larger number of irradiation field sizes are actually preset finely and scan paths corresponding to the preset irradiation field sizes are prepared previously. The sequences of the scanning magnet excitation current values shown in FIG. 13, corresponding to the plurality of raster scan paths, are stored in the memory of the overall control apparatus 102 of the particle therapy system while associating the sequences with the irradiation field sizes.

The treatment planning apparatus 104 sends information on the irradiation field size of each layer to the overall control apparatus 102. Based on the irradiation field size information on each layer sent from the treatment planning apparatus, the overall control apparatus 102 selects a raster scan path corresponding to the irradiation field size from the plurality of raster scan paths registered in the memory and sends the sequences of the scanning magnet excitation current values for the selected scan path to the scanning magnet power supply control unit 71.

With the above operation, it becomes possible to carry out the lateral irradiation of each layer with the minimum scan path covering the multi-leaf collimator aperture area of each layer. Thus, similarly to the third embodiment, the treatment time can be reduced thanks to the shortening of the scan path for each layer and the charged particle beam transported to the irradiation nozzle can be utilized with higher efficiency compared to the conventional technique.

Incidentally, while square irradiation fields have been assumed as the irradiation field sizes in this embodiment, the irradiation field sizes may also be circular. For example, the irradiation field sizes may be specified as 10 cm, 15 cm and 20 cm in diameter and raster scan paths corresponding to these irradiation field sizes (diameters) may be prepared.

Fifth Embodiment

A fifth embodiment as another preferred embodiment of the present invention will be described referring to figures. This embodiment describes a case where each layer of the layer-partitioned target volume in the conformal layer stacking irradiation is irradiated and scanned in the lateral directions by means of the zigzag scan.

In the conventional conformal layer stacking irradiation, every layer was irradiated using the zigzag scan path 603 shown in FIG. 8. FIG. 15A shows a zigzag scan path 603 for the most distal layer (layer 1) in this embodiment, and FIG. 15B shows a zigzag scan path 603 for the layer 6 situated at a more proximal (shallower) position. In FIGS. 15A and 15B, the zigzag scan path for the layer 6 is shortened compared to that for the layer 1 since the multi-leaf collimator aperture area is reduced. Similarly to the third embodiment, each zigzag scan path shown in FIGS. 15A and 15B is calculated as the minimum scan path by the treatment planning apparatus 104 after calculating the multi-leaf collimator aperture for each layer of the layer-partitioned target volume.

A method for calculating the zigzag scan path 603 that is employed by the treatment planning apparatus 104 will be explained below. First, the ranges of the multi-leaf collimator aperture area of each layer in the X direction and in the Y direction are determined. The beam size σ is determined as 2 cm, for example. The interval between the oblique scan lines and the number of scan lines constituting the zigzag scan are determined from the range of the aperture area in the Y direction. The scan range in the X direction is determined considering the drop in the dose distribution at both ends resulting from the continuous irradiation with the charged particle beam. The calculation of the zigzag scan path is conducted for the multi-leaf collimator aperture area of each layer.

The sequences of the scanning magnet excitation current values in this embodiment are similar to those shown in FIG. 13. Also in the zigzag scan, the scanning is conducted like the one-stroke drawing without turning the beam OFF similarly to the raster scan. The scanning magnet excitation current value sequences for each layer, like those shown in FIG. 13, are stored in the memory of the overall control apparatus 102 and the irradiation of each layer is carried out according to the stored sequences similarly to the raster scan in the third embodiment.

Also in the zigzag scan, a method previously preparing a plurality of zigzag scan paths corresponding to various irradiation field sizes may also be employed as in the fourth embodiment. Since the treatment planning apparatus 104 sends the calculated irradiation field size of each layer of the layer-partitioned target volume to the overall control apparatus 102, a corresponding zigzag scan path is selected from the prepared zigzag scan paths based on the information. For example, a plurality of zigzag scan paths corresponding to the irradiation field sizes shown in FIGS. 14A, 14B and 14C may be formed previously.

Sixth Embodiment

A sixth embodiment as another preferred embodiment of the present invention will be described referring to figures. This embodiment describes a case where each layer of the layer-partitioned target volume in the conformal layer stacking irradiation is irradiated and scanned in the lateral directions by means of the circular wobbling.

In the conventional conformal layer stacking irradiation, every layer was irradiated using the circular wobbling scan path 604 shown in FIG. 9. FIG. 16A shows a circular wobbling scan path 604 for the most distal layer (layer 1) in this embodiment, and FIG. 16B shows a circular wobbling scan path 604 for the layer 6 situated at a more proximal (shallower) position. In FIGS. 16A and 16B, the circular wobbling scan path for the layer 6 has a smaller wobbling radius compared to the circular wobbling scan path for the layer 1 since the multi-leaf collimator aperture area is reduced. Similarly to the third embodiment, each scan path shown in FIGS. 16A and 16B is calculated by the treatment planning apparatus 104 as the minimum scan path (minimum wobbling radius) based on the multi-leaf collimator aperture for each layer of the layer-partitioned target volume.

A method for calculating the circular wobbling scan path 604 that is employed by the treatment planning apparatus 104 will be explained below. First, the radius of a circle (circular area) covering the multi-leaf collimator aperture area of each layer is determined. The wobbling radius of the circular wobbling is set at approximately 1.4 times the radius of the circle. The uniform irradiation of the collimator aperture area is possible by setting the beam size at approximately 0.6-0.7 times the wobbling radius of the circular wobbling. In cases where the wobbling radius is gradually reduced for the irradiation of more proximal (shallower) layers, the beam size is also reduced corresponding to the wobbling radius by changing the level of insertion of the scatterer in order to keep the uniformity of the dose distribution.

The sequences of the scanning magnet excitation current values in this embodiment for the circular wobbling are similar to those shown in FIG. 13. The sequences for each layer, like those shown in FIG. 13, are stored in the memory of the overall control apparatus 102 and the irradiation of each layer is carried out according to the stored sequences similarly to the raster scan in the third embodiment.

Also in the circular wobbling, a method previously preparing a plurality of circular wobbling scan paths corresponding to various irradiation field sizes may also be employed as in the fourth embodiment. Since the treatment planning apparatus 104 sends the calculated irradiation field size of each layer of the layer-partitioned target volume to the overall control apparatus 102, a corresponding circular wobbling scan path is selected from the prepared circular wobbling scan paths based on the information. For example, a plurality of circular wobbling scan paths corresponding to the irradiation field sizes shown in FIGS. 14A, 14B and 14C may be formed previously.

Seventh Embodiment

A seventh embodiment as another preferred embodiment of the present invention will be described referring to figures. This embodiment describes a case where each layer of the layer-partitioned target volume in the conformal layer stacking irradiation is irradiated and scanned in the lateral directions by means of the spiral wobbling.

In the conventional conformal layer stacking irradiation, every layer was irradiated using the spiral wobbling scan path 605 shown in FIG. 10. FIG. 17A shows a spiral wobbling scan path 605 for the most distal layer (layer 1) in this embodiment, and FIG. 17B shows a spiral wobbling scan path 605 for the layer 6 situated at a more proximal (shallower) position. In FIGS. 17A and 17B, the spiral wobbling scan path for the layer 6 has a smaller maximum radius compared to the spiral wobbling scan path for the layer 1 since the multi-leaf collimator aperture area is reduced. Similarly to the third embodiment, each scan path shown in FIGS. 17A and 17B is calculated by the treatment planning apparatus 104 by calculating the maximum radius of the spiral wobbling based on the multi-leaf collimator aperture for each layer of the layer-partitioned target volume.

A method for calculating the spiral wobbling scan path 605 that is employed by the treatment planning apparatus 104 will be explained below. First, the radius of a circle (circular area) covering the multi-leaf collimator aperture area of each layer is determined. The beam size σ is determined as 2 cm, for example. The maximum radius of the spiral wobbling may be set at a value obtained by adding approximately twice the beam size to the radius of the circle, by which the aperture area can be irradiated with a uniform dose distribution.

The sequences of the scanning magnet excitation current values in this embodiment for the spiral wobbling are similar to those shown in FIG. 13. The sequences for each layer, like those shown in FIG. 13, are stored in the memory of the overall control apparatus 102 and the irradiation of each layer is carried out according to the stored sequences similarly to the raster scan in the third embodiment.

Also in the spiral wobbling, a method previously preparing a plurality of spiral wobbling scan paths corresponding to various irradiation field sizes may also be employed as in the fourth embodiment. Since the treatment planning apparatus 104 sends the calculated irradiation field size of each layer of the layer-partitioned target volume to the overall control apparatus 102, a corresponding spiral wobbling scan path is selected from the prepared spiral wobbling scan paths based on the information. For example, a plurality of spiral wobbling scan paths corresponding to the irradiation field sizes shown in FIGS. 14A, 14B and 14C may be formed previously.

Eighth Embodiment

An eighth embodiment as another preferred embodiment of the present invention will be described referring to figures. This embodiment describes a case where each layer of the layer-partitioned target volume in the conformal layer stacking irradiation is irradiated and scanned in the lateral directions by means of the line scan.

In the conventional conformal layer stacking irradiation, every layer was irradiated using the line scan path 601 shown in FIG. 11. FIG. 18A shows a line scan path 601 for the most distal layer (layer 1) in this embodiment, and FIG. 18B shows a line scan path 601 for the layer 6 situated at a more proximal (shallower) position. The present invention focuses on the fact that the shape of the target volume extending in the lateral directions (when each layer of the layer-partitioned target volume is viewed in the beam propagation direction) gradually becomes smaller in more proximal (shallower) layers. Thus, also the multi-leaf collimator aperture area gradually becomes smaller in more proximal layers compared to the most distal (deepest) layer. Therefore, compared to the scan path for irradiating the most distal layer 1, the scan path for irradiating the proximal layer 6 can be shortened as shown in FIGS. 18A and 18B so that only the reduced multi-leaf collimator aperture area can be irradiated uniformly. Since the multi-leaf collimator aperture area of each layer has been calculated by the treatment planning apparatus 104, the treatment planning apparatus calculates the minimum scan path with which the aperture area can be irradiated with a uniform dose distribution, according to the multi-leaf collimator aperture area of each layer.

A method for calculating the line scan path 601 that is employed by the treatment planning apparatus 104 will be explained below. First, the ranges of the multi-leaf collimator aperture area in the X direction and in the Y direction are determined. The beam size σ of the charged particle beam is determined as 2 cm, for example. The number of scan lines arranged in the Y direction is determined by setting the scan interval in the Y direction (see FIG. 11) as an element constituting the line scan path. For example, assuming that the range of the aperture area in the Y direction is a 10 cm range from −5 cm to +5 cm, the scan interval is set at 3.5 cm (less than twice the beam size) and the number of scan lines is set at 5. The scan range in the X direction is determined for each scan line in the X direction, considering the range of the aperture area in the X direction at the scan line and the drop in the dose distribution at both ends which varies depending on the beam size. The line scan path is calculated and determined for each layer as above since the multi-leaf collimator aperture area varies from layer to layer.

After calculating the optimum scan path for each layer, the treatment planning apparatus 104 transmits the result of the calculation to the overall control apparatus 102 of the particle therapy system. The overall control apparatus 102 converts the coordinate values of the scan path into the excitation current values for the horizontal and vertical scanning magnets 41A and 41B. Since the line scan requires the beam control (beam-on, beam-off) for each scan line, the beam control information is added to the sequences of the excitation current values corresponding to the scan path. FIG. 19 shows the sequences of the scanning magnet excitation current values and the beam control information calculated as above. The information shown in FIG. 19 is stored as a table in the memory of the overall control apparatus 102. The overall control apparatus 102 sends the information on the excitation current values to the scanning magnet power supply control unit 71 successively from the top of the table shown in FIG. 19, while also sending the beam control signals to the accelerator/beam transport system control apparatus 101.

With the above operation, in the conformal layer stacking irradiation employing the line scan for the charged particle beam scanning in the lateral directions, it becomes possible to carry out the irradiation using the minimum scan path that uniformly irradiates only the multi-leaf collimator aperture area of each layer of the layer-partitioned target volume. Thanks to the shortening of the scan path compared to the conventional conformal layer stacking irradiation, the treatment time can be reduced from that in the conventional technique. Since the irradiation of each layer is conducted using the minimum scan path, the amount of the charged particle beam irradiating the screening part of the multi-leaf collimator in the conventional conformal layer stacking irradiation can be reduced, by which the charged particle beam transported to the irradiation nozzle can be utilized with higher efficiency compared to the conventional technique.

Also in the line scan, a method that previously prepares a plurality of line scan paths corresponding to various irradiation field sizes may also be employed as in the fourth embodiment. Since the treatment planning apparatus 104 sends the calculated irradiation field size of each layer of the layer-partitioned target volume to the overall control apparatus 102, a corresponding line scan path is selected from the prepared line scan paths based on the information. For example, a plurality of line scan paths corresponding to the irradiation field sizes shown in FIGS. 14A, 14B and 14C may be formed previously.

What is claimed is:

1. A treatment planning apparatus for planning a uniform scan in which a dose distribution uniform in lateral directions is formed by scanning a charged particle beam with electromagnets, wherein:
the treatment planning apparatus comprises a treatment planning operation unit that determines a shape of a collimator aperture in accordance with a shape of a target volume, and then calculates an optimum scan path in the lateral directions in consideration of the collimator aperture determined in accordance with the shape of the target volume such that only an area of the collimator aperture is to be irradiated with the uniform dose distribution, and said uniform scan is planned such that an irradiation field is painted with the charged particle beam having a size smaller than the irradiation field.

2. The treatment planning apparatus according to claim 1, wherein the scan path in the lateral directions is a raster scan path.

3. The treatment planning apparatus according to claim 1, wherein the scan path in the lateral directions is a line scan path.

4. A treatment planning apparatus for planning conformal layer stacking irradiation in which a target volume is partitioned into layers, a bolus for adjusting the dose distribution to the shape of the target volume is used, and each layer of the layer-partitioned target volume is successively irradiated with a charged particle beam while changing an irradiation field shape in lateral directions for each layer by using a multi-leaf collimator, wherein:
the treatment planning apparatus comprises a treatment planning operation unit that determines a shape of a collimator aperture in accordance with a shape of the target volume, then changes the scan path of the charged particle beam for each layer by calculating a multi-leaf collimator aperture area of each layer in accordance with the shape of the target volume such that only the multi-leaf collimator aperture area of each layer is to be irradiated with a uniform dose distribution and calculating a minimum scan path of the charged particle beam suitable for the multi-leaf collimator aperture area of each layer, and
said conformal layer stacking irradiation is planned such that the irradiation field is painted with the charged particle beam having a size smaller than the irradiation field.

5. The treatment planning apparatus according to claim 4, wherein the lateral irradiation of each layer is conducted by means of the raster scan.

6. The treatment planning apparatus according to claim 4, wherein the lateral irradiation of each layer is conducted by means of the zigzag scan.

7. The treatment planning apparatus according to claim 4, wherein the lateral irradiation of each layer is conducted by means of the spiral wobbling.

8. The treatment planning apparatus according to claim 4, wherein the lateral irradiation of each layer is conducted by means of the line scan.

9. A particle therapy system for conducting conformal layer stacking irradiation in which a target volume is partitioned into layers, a bolus for adjusting the dose distribution to a shape of the target volume is used, and each layer of the layer-partitioned target volume is successively irradiated with a charged particle beam while changing an irradiation field shape in lateral directions for each layer using a multi-leaf collimator, wherein: the particle therapy system comprises:
a treatment planning apparatus that determines a shape of a collimator multi-leaf collimator aperture in accordance with the shape of the target volume, then calculates a multi-leaf collimator aperture area of each layer and calculates an irradiation field size covering the calculated multi-leaf collimator aperture area of each layer, and
a control apparatus that previously holds a plurality of scan paths corresponding to the calculated irradiation field sizes and changes the scan path of the charged particle beam for each layer based on the scan path corresponding to the calculated irradiation field size so that only the calculated multi-leaf collimator aperture area of each layer is to be irradiated with a uniform dose distribution, wherein said conformal layer stacking irradiation is made such that the irradiation field is painted with the charged particle beam having a size smaller than the irradiation field.

10. The particle therapy system according to claim 9, wherein the lateral irradiation of each layer is conducted by means of the raster scan.

11. The particle therapy system according to claim 9, wherein the lateral irradiation of each layer is conducted by means of the zigzag scan.

12. The particle therapy system according to claim 9, wherein the scan path for each layer is a minimum scan path corresponding to the calculated irradiation field size.

13. The particle therapy system according to claim 9, wherein the lateral irradiation of each layer is conducted by means of the spiral wobbling.

14. The particle therapy system according to claim 9, wherein the lateral irradiation of each layer is conducted by means of the line scan.

* * * * *